US009579337B2

(12) United States Patent
Stover et al.

(10) Patent No.: US 9,579,337 B2
(45) Date of Patent: Feb. 28, 2017

(54) USE OF URIDINE AND DEOXYURIDINE TO TREAT FOLATE-RESPONSIVE PATHOLOGIES

(75) Inventors: Patrick J. Stover, Ithaca, NY (US); Martha S. Field, Burdett, NY (US)

(73) Assignee: Cornell University, Ithaca, NY (US)

( * ) Notice: Subject to any disclaimer, the term of this patent is extended or adjusted under 35 U.S.C. 154(b) by 235 days.

(21) Appl. No.: 14/113,858

(22) PCT Filed: Apr. 25, 2012

(86) PCT No.: PCT/US2012/034963
§ 371 (c)(1),
(2), (4) Date: Dec. 5, 2013

(87) PCT Pub. No.: WO2012/148998
PCT Pub. Date: Nov. 1, 2012

(65) Prior Publication Data
US 2014/0080784 A1 Mar. 20, 2014

Related U.S. Application Data

(60) Provisional application No. 61/478,669, filed on Apr. 25, 2011, provisional application No. 61/515,356, filed on Aug. 5, 2011.

(51) Int. Cl.
*A61K 31/7072* (2006.01)
*A23L 33/13* (2016.01)
*A61N 5/10* (2006.01)
*A61K 45/06* (2006.01)

(52) U.S. Cl.
CPC ............ *A61K 31/7072* (2013.01); *A23L 33/13* (2016.08); *A61K 45/06* (2013.01); *A61N 5/10* (2013.01)

(58) Field of Classification Search
CPC .............................. A61K 31/7072; A23L 33/13
See application file for complete search history.

(56) References Cited

U.S. PATENT DOCUMENTS

| | | | | |
|---|---|---|---|---|
| 4,434,788 A | * | 3/1984 | Nakatsugawa | A61K 31/70 514/45 |
| 2002/0049163 A1 | | 4/2002 | Cook et al. | |
| 2006/0280776 A1 | * | 12/2006 | Koide | A23L 33/20 424/439 |
| 2007/0114476 A1 | | 5/2007 | Williams | |

FOREIGN PATENT DOCUMENTS

| | | |
|---|---|---|
| CN | 101019880 A | 8/2007 |
| WO | 2008003514 A2 | 1/2008 |
| WO | 2009/002146 A1 | 12/2008 |

OTHER PUBLICATIONS

Czeizel et al., N. Engl. J. Med., 1992, 327, p. 1832-1835.*
Copp et al., Indian J. Pediatr., 2000, 67(12), p. 915-921.*
Pelliniemi et al., J. Clin. Invest., 1980, 65, p. 449-460.*
Mamel et al., Nutr. Clin. Pract., 1998, 13(3), p. 123-128.*
Dunlevy et al., "Abnormal Folate Metabolism in Foetuses Affected by Neural Tube Defects," Brain 130:1043-1049 (2007).
Stover, "One-Carbon Metabolism-Genome Interactions in Folate-Associated Pathologies," J. Nutr. 139:2402-2405 (2009).
Bannigan, "The Effects of 5-Bromodeoxyuridine on Fusion of the Cranial Neural Folds in the Mouse Embryo," Teratology 32:229-239 (1985).
Supplementary Partial European Search Report for corresponding EP 12777418.0 (Dec. 3, 2014).
Shane, "Folate Chemistry and Metabolism," in Bailey, ed., Folate in Health and Disease, New York, New York:Marcel Dekker, Inc., pp. 1-24 (1995).
Fox et al., "Folate-Mediated One-Carbon Metabolism," Vitam Horm. 79: 1-44 (2008).
James et al., "Diet-Induced DNA Damage and Altered Nucleotide Metabolism in Lymphocytes from Methyl-Donor-Deficient Rats," Carcinogenesis 10(7): 1209-1214 (1989).
Branda et al., "Folate Deficiency Increases Genetic Damage Caused by Alkylating Agents and Gamma-Irradiation in Chinese Hamster Ovary Cells," Cancer Res. 53(22):5401-5408 (1993).
Duthie et al., "DNA Instability (Strand Breakage, Uracil Misincorporation, and Defective Repair) Is Increased by Folic Acid Depletion in Human Lymphocytes in Vitro," Faseb. J. 12(14):1491-1497 (1998).
Wainfan et al., "Methyl Groups in Carcinogenesis: Effects on DNA Methylation and Gene Expression," Cancer Res. 52(7 Suppl):2071s-2077s (1992).
Friso et al., "A Common Mutation in the 5,10-Methylenetetrahydrofolate Reductase Gene Affects Genomic DNA Methylation Through an Interaction With Folate Status," Proc. Nat'l. Acad. Sci. U.S.A. 99(8):5606-5611 (2002).
Gaudet et al., "Induction of Tumors in Mice by Genomic Hypomethylation," Science 300 (5618): 489-492 (2003).
Herbig et al., "Cytoplasmic Serine Hydroxymethyltransferase Mediates Competition Between Folate-Dependent Deoxyribonucleotide and S-adenosylmethionine Biosyntheses," J. Biol. Chem. 277(41)38381-38389 (2002).

(Continued)

*Primary Examiner* — Jonathan S Lau
(74) *Attorney, Agent, or Firm* — LeClairRyan, a Professional Corporation

(57) ABSTRACT

The present invention relates to a pharmaceutical or dietary composition comprising deoxyuridine and a pharmaceutically or dietetically suitable carrier. Another aspect of the present invention relates to a method of supplementing the dietary needs of a subject. This method includes administering to the subject a dietary supplementing effective amount of deoxyuridine. Yet another aspect of the present invention relates to a method of treating cancer in a subject. This method includes selecting a subject having cancer and administering to the selected subject a therapeutically effective amount of uridine, thereby treating the cancer in the selected subject.

14 Claims, 5 Drawing Sheets

(56) References Cited

OTHER PUBLICATIONS

Woeller et al., "Evidence for Small Ubiquitin-Like Modifier-Dependent Nuclear Import of the Thymidylate Biosynthesis Pathway," including supplemental data, J. Biol. Chem. 282(24):17623-17631 (2007).

MacFarlane et al., "Cytoplasmic Serine Hydroxymethyltransferase Regulates the Metabolic Partitioning of Methylenetetrahydrofolate But Is Not Essential in Mice," J. Biol. Chem. 283(38):25846-25853 (2008).

Extended European Search Report for corresponding EP Application No. 12777418.0 (Apr. 30, 2015).

First Office Action for corresponding CN Application No. 201280031365.X (Apr. 2, 2015).

Beaudin et al., "Shmt1 and De Novo Thymidylate Biosynthesis Underlie Folate-Responsive Neural Tube Defects in Mice," with Supplemental Material, Am. J. Clin. Nutr. 93:789-798 (Feb. 23, 2011).

MacFarlane et al., "Shmt1 Heterozygosity Impairs Folate-Dependent Thymidylate Synthesis Capacity and Modifies Risk of Apc min-Mediated Intestinal Cancer Risk," with Supplementary Data, Cancer Research 71(6):2098-2107 (Mar. 15, 2011).

PCT International Search Report and Written Opinion for corresponding PCT/US2012/034963, 8 pages (mailed Jul. 27, 2012).

\* cited by examiner

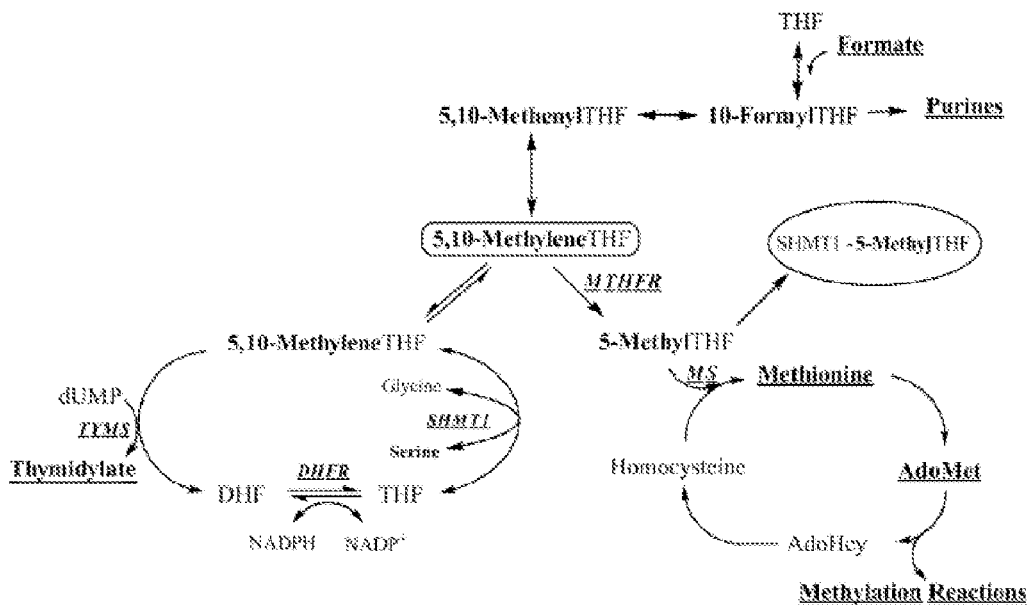

*FIG. 1*

Table: Experimental Diets

| Diet abbreviation | Full diet description |
|---|---|
| C | AIN-93G purified rodent diet, with sterile Casein, folic acid and choline bitartrate, gamma irradiated |
| FD | AIN-93G purified rodent diet with sterile Casein, without folic acid, with choline bitartrate, gamma irradiated |
| C+U | AIN-93G purified rodent diet, with sterile Casein, folic acid and choline bitartrate, gamma irradiated, with 0.6% uridine (Sigma, # U3750), gamma irradiated |
| FD+U | AIN-93G purified rodent diet with sterile Casein without folic acid, with choline bitartrate, with 0.6% uridine (Sigma, # U3750), gamma irradiated |
| C+T | AIN-93G purified rodent diet, with sterile Casein, folic acid and choline bitartrate, with 0.2% thymidine (Sigma, # T9250), gamma irradiated |
| FD+T | AIN-93G purified rodent diet, with sterile Casein, without folic acid, with choline bitartrate, with 0.2% thymidine (Sigma, # T9250), gamma irradiated |
| C+dU | AIN-93G purified rodent diet with sterile Casein, folic acid and choline bitartrate, gamma irradiated, with 0.1% 2′-Deoxyuridine (Sigma, # D5412), gamma irradiated |
| FD+dU | AIN-93G purified rodent diet, with sterile Casein, without folic acid, with choline bitartrate, with 0.1% 2′-Deoxyuridine (Sigma, #D5412), gamma irradiated |

*FIG. 2*

**Table: Number of implants, viable embryos, dead embryos and frequency of neural tube defects (NTDs) in *Shmt1*-defficient embryos on a 129/SvEv background as a function of maternal *Shmt1* genotype and diet.**

| Diet and maternal genotype | No. of litters | No. of implants | No. of viable embryos | No. of dead embryos[f] (%) | No. of resorptions[g] | No. of NTDs (%)[3,4] | CR Length (mm)[5] |
|---|---|---|---|---|---|---|---|
| C | | | | | | | |
|   *Shmt1*[+/−] | 11 | 71 | 67 | 4 (5.6) | 3 | 0 | 8.17 ± 0.2 |
|   *Shmt1*[−/−] | 10 | 58 | 53 | 5 (8.6) | 16 | 0 | 8.13 ± 0.3 |
| FD | | | | | | | |
|   *Shmt1*[+/−] | 11 | 47 | 42 | 5 (10.6) | 33 | 1 (2.4)[a] | 6.92 ± 0.3[5a] |
|   *Shmt1*[−/−] | 10 | 56 | 47 | 9 (16.1) | 15 | 5 (10.6)[b] | 6.58 ± 0.3 |
| C+U | | | | | | | |
|   *Shmt1*[+/−] | 13 | 76 | 69 | 7 (9.2) | 11 | 4 (5.8)[c] | 7.48 ± 0.2 |
|   *Shmt1*[−/−] | 10 | 54 | 50 | 4 (7.4) | 13 | 3 (6)[d] | 7.32 ± 0.3 |
| FD+U | | | | | | | |
|   *Shmt1*[+/−] | 10 | 60 | 56 | 4 (6.7) | 13 | 3 (5.4)[e] | 7.35 ± 0.3 |
|   *Shmt1*[−/−] | 11 | 56 | 44 | 12 (21.4) | 15 | 7 (15.9)[f] | 6.96 ± 0.3 |
| C+T | | | | | | | |
|   *Shmt1*[+/−] | 12 | 66 | 59 | 7 (10.6) | 7 | 0 | 7.21 ± 0.3 |
|   *Shmt1*[−/−] | 11 | 64 | 60 | 4 (6.3) | 5 | 0 | 7.25 ± 0.3 |
| FD+T | | | | | | | |
|   *Shmt1*[+/−] | 11 | 52 | 49 | 3 (5.8) | 15 | 2 (4.1)[g] | 7.10 ± 0.3 |
|   *Shmt1*[−/−] | 10 | 40 | 32 | 8 (20) | 18 | 3 (9.4)[h] | 7.32 ± 0.3 |
| C+dU | | | | | | | |
|   *Shmt1*[+/−] | 10 | 54 | 40 | 14 (26) | 24 | 0 | 6.82 ± 0.2[5a] |
|   *Shmt1*[−/−] | 11 | 59 | 54 | 5 (8.5) | 17 | 0 | 7.18 ± 0.2 |
| FD+dU | | | | | | | |
|   *Shmt1*[+/−] | 11 | 42 | 38 | 4 (9.5) | 24 | 0 | 7.81 ± 0.3 |
|   *Shmt1*[−/−] | 13 | 61 | 49 | 12 (19.7) | 24 | 0 | 7.21 ± 0.2 |
| P value | | | | | | | |
| Diet effect | | | | NS | < 0.05 | P < 0.0001 | 0.0001 |
| Genotype effect | | | | NS | NS | NS | NS |
| Diet x Genotype effect | | | | NS | NS | NS | 0.05 |

*FIG. 3*

Table: Frequency of NTDs in embryos as a function of maternal diet.[1]

| Diet and maternal genotype | Embryonic genotype | | |
|---|---|---|---|
| | $Shmt1^{+/+}$ | $Shmt1^{+/-}$ | $Shmt1^{-/-}$ |
| C | | | |
| No of Embryos | 31 | 62 | 27 |
| No of NTDs | 0 | 0 | 0 |
| No of dead NTDs | 0 | 0 | 0 |
| FD | | | |
| No of Embryos | 21 | 49 | 19 |
| No of NTDs | 0 | 6 (12.2%)[2,3] | 0 |
| No of dead NTDs | 0 | 0 | 2 |
| C+U | | | |
| No of Embryos | 35 | 58 | 26 |
| No of NTDs | 1 (2.9%) | 5 (8.6%) | 1 (3.8%) |
| No of dead NTDs | 0 | 1 | 0 |
| FD+U | | | |
| No of Embryos | 25 | 56 | 19 |
| No of NTDs | 1 (4%) | 5 (8.9%) | 4 (21.1%) |
| No of dead NTDs | 1 | 0 | 2 |
| C+T | | | |
| No of Embryos | 24 | 63 | 32 |
| No of NTDs | 0 | 0 | 0 |
| No of dead NTDs | 0 | 0 | 0 |
| FD+T | | | |
| No of Embryos | 23 | 45 | 13 |
| No of NTDs | 1 (4.3%) | 2 (4.4%) | 2 (15.4%) |
| No of dead NTDs | 0 | 0 | 0 |
| C+dU | | | |
| No of Embryos | 17 | 50 | 27 |
| No of NTDs | 0 | 0 | 0 |
| No of dead NTDs | 0 | 0 | 0 |
| FD+dU | | | |
| No of Embryos | 18 | 51 | 18 |
| No of NTDs | 0 | 0 | 0 |
| No of dead NTDs | 0 | 0 | 0 |

[1] The effect of embryonic Shmt1 genotype and maternal diets were assessed by using a modified generalized linear model procedure. The frequency of exencephaly (NTDs) occurrence for $Shmt1^{-/-}$ mothers' genotype ($\chi^2 = 43.565$, $P < 0.0001$); and did not affect significantly $Shmt1^{+/+}$ mothers' genotype ($P = 0.21$ not significant (NS)).

[2] Percentages of NTDs to viable embryos.

[3] $P = 0.0011$; $\chi^2 = 22.23$ for the number of NTDs in embryos isolated from dams fed the FD+U diet compared to viable embryos fed the FD+U diet.
$P = 0.0469$; $\chi^2 = 12.77$ for the number of NTDs in embryos isolated from dams fed the C+U diet compared to viable embryos fed the C+U diet.
$P = 0.0233$; $\chi^2 = 7.52$ for the number of NTDs in embryos isolated from dams fed the FD diet compared to viable embryos fed the FD diet.

*FIG. 4*

Table: Metabolites Levels of *Shmt1*[+/+] and *Shmt1*[-/-] Females:

*Shmt1*[+/+]

| | \multicolumn{6}{c|}{Maternal Diet} | \multicolumn{3}{c|}{P value} |
|---|---|---|---|---|---|---|---|---|---|
| | C | FD | C+U | C+dU | C+T | FD+U | FD+dU | FD+T | Diet | Gene | DxG |
| Folate (fmol/uL) | 170.78 ± 27.7 | < 10 | 180.47 ± 27.7 | 272.28 ± 27.7 | 263.51 ± 50.5 | < 10 | < 10 | < 10 | <0.0001[a] | NS | NS |
| Glucose (mg/dL) | 126.57 ± 4.9 | 145.00 ± 5.3 | 168.17 ± 5.3[b] | 127.28 ± 4.9 | 146.00 ± 4.1 | 141.50 ± 4.6[b] | 132.78 ± 4.3 | 133.50 ± 4.1 | <0.0001[b] | NS | NS |
| Uracil (pg/ug DNA) | 0.23 ± 0.02 | 0.18 ± 0.03 | 0.17 ± 0.03 | 0.18 ± 0.03 | 0.21 ± 0.03 | 0.20 ± 0.03 | 0.17 ± 0.03 | 0.16 ± 0.03 | NS | 0.0144[c] | NS |
| Uridine (uM) | 7.87 ± 1.4 | 4.87 ± 1.5 | 5.56 ± 1.7 | 5.91 ± 1.4 | 11.35 ± 1.6 | 13.22 ± 1.6 | 8.69 ± 1.5 | 11.20 ± 2.0 | 0.0014[d] | 0.039[e] | S[f] |
| Thymidine (uM) | 1.43 ± 0.2 | 0.73 ± 0.2 | 0.78 ± 0.3 | 1.12 ± 0.2 | 1.25 ± 0.2 | 0.85 ± 0.2 | 1.15 ± 0.2 | 0.79 ± 0.3 | NS | NS | NS |
| Deoxyuridine (uM) | 1.60 ± 0.2 | 1.54 ± 0.2 | 1.54 ± 0.3 | 2.10 ± 0.2 | 1.97 ± 0.3 | 1.89 ± 0.2 | 1.62 ± 0.2 | 1.67 ± 0.3 | <0.0001[g] | NS | 0.0096[h] |

*Shmt1*[-/-]

| | \multicolumn{6}{c|}{Maternal Diet} | \multicolumn{3}{c|}{p value} |
|---|---|---|---|---|---|---|---|---|---|
| | C | FD | C+U | C+dU | C+T | FD+U | FD+dU | FD+T | Diet | Gene | DxG |
| Folate (fmol/uL) | 159.45 ± 24.0 | < 10 | 146.02 ± 29.3 | 253.30 ± 29.3 | 258.01 ± 34.7 | < 10 | < 10 | < 10 | <0.0001[a] | NS | NS |
| Glucose (mg/dL) | 124.60 ± 5.8 | 141.00 ± 6.5 | 154.40 ± 4.1[b] | 130.67 ± 4.3 | 128.00 ± 4.3 | 149.83 ± 5.3[b] | 127.38 ± 4.6 | 137.67 ± 4.3 | <0.0001[b] | NS | NS |
| Uracil (pg/ug DNA) | 0.24 ± 0.03 | 0.24 + 0.03 | 0.20 + 0.03 | 0.19 + 0.03 | 0.21 + 0.03 | 0.23 + 0.03 | 0.23 + 0.02 | 0.26 + 0.04 | NS | 0.0144[c] | NS |
| Uridine (uM) | 8.57 ± 1.6 | 4.84 ± 1.6 | 5.81 ± 1.6 | 3.97 ± 2.0 | 8.13 ± 1.7 | 5.52 ± 1.4 | 8.53 ± 1.4 | 9.80 ± 1.7 | 0.0014[d] | 0.039[e] | S[f] |
| Thymidine (uM) | 1.03 ± 0.3 | 1.04 ± 0.2 | 1.24 ± 0.3 | 1.09 ± 0.3 | 0.82 ± 0.2 | 0.85 ± 0.2 | 1.07 ± 0.2 | 1.82 ± 0.3 | NS | NS | NS |
| Deoxyuridine (uM) | 1.44 ± 0.3 | 1.77 ± 0.2 | 1.48 ± 0.2 | 3.45 ± 0.3 | 2.22 ± 0.2 | 1.24 ± 0.2 | 2.24 ± 0.2 | 1.82 ± 0.3 | <0.0001[g] | NS | 0.0096[h] |

DxG = diet x genotype effect, Gene = genotype a: Folate levels were significantly different by diet; diets based on FD, were F = 58.3526, $P < 0.0001$; all compared to C; C+dU and C +T were also significantly different ($P < 0.05$) from C diet. The only C+U diet was not significantly different from C diet; all according to Tukey HSD.

b: Glucose levels were significantly different by diet. C+U and FD +U were significantly higher ($P < 0.05$) compared to C diet, but also compared to C+dU and FD+dU by using Tukey HSD by diet; F = 11.478; $P < 0.0001$.

c: Uracil levels were significantly different by gene only: F = 6.7414; $P = 0.0114$; *Shmt1*[-/-] 0.22 ± 0.01 ; *Shmt1*[+/+] 0.19 ± 0.01 (Mean ± SEM).

d: Uridine levels were significantly different by diet: F = 3.7552; $P = 0.0014$ in general. According to Tukey HSD test, FD+T vs FD diets were significantly different by diet $P < 0.05$.

e: Uridine levels were significantly different by gene: F = 4.4011; $P = 0.039$ in general; *Shmt1*[-/-] 6.90 ± 0.6; *Shmt1*[+/+] 8.59 ± 0.6 (Mean ± SEM)

f: Uridine levels were significantly different by interaction of gene and diet according to Tukey HSD test: *Shmt1*[-/-] FD – U diet was significantly different ($P < 0.05$) from groups : *Shmt1*[-/-] FD – U; *Shmt1*[-/-] FD, *Shmt1*[-/-] FD; *Shmt1*[-/-] C+dU g: Deoxyuridine levels were significantly different by diet: F= 5.638, $P < 0.0001$: according to Tukey HSD test ($P < 0.05$) Deoxyuridine levels were significantly different on C+dU from all diets besides C+T.

h: Deoxyuridine levels were significantly different by interaction of gene and diet F= 2.8768, $P = 0.0096$.

According to Tukey HSD test ($P < 0.05$). *Shmt1*[-/-] C+dU diet was significantly different ($P < 0.05$) from all groups besides *Shmt1*[-/-] C+T, and *Shmt1*[-/-] FD+dU Blood glucose levels in pregnant females measured at the day of embryonic harvest with no fast. Values are mean ± SEM from at least three to ten mice per group. $P \leq 0.05$ between genotypes and diets

*FIG. 5*

SEQUENCE LISTING

```
<160> NUMBER OF SEQ ID NOS: 5

<210> SEQ ID NO 1
<211> LENGTH: 19
<212> TYPE: DNA
<213> ORGANISM: Artificial
<220> FEATURE:
<223> OTHER INFORMATION: Primer

<400> SEQUENCE: 1
gacactgttc acatccctc                                                 19

<210> SEQ ID NO 2
<211> LENGTH: 19
<212> TYPE: DNA
<213> ORGANISM: Artificial
<220> FEATURE:
<223> OTHER INFORMATION: Primer

<400> SEQUENCE: 2
caaaacattc gggagcctc                                                 19

<210> SEQ ID NO 3
<211> LENGTH: 18
<212> TYPE: DNA
<213> ORGANISM: Artificial
<220> FEATURE:
<223> OTHER INFORMATION: Primer

<400> SEQUENCE: 3
gccatccctt cacgttag                                                  18
```

```
<210> SEQ ID NO 4
<211> LENGTH: 21
<212> TYPE: DNA
<213> ORGANISM: Artificial
<220> FEATURE:
<223> OTHER INFORMATION: Primer

<400> SEQUENCE: 4
ttctgagaaa gacagaagtt a                                              21

<210> SEQ ID NO 5
<211> LENGTH: 19
<212> TYPE: DNA
<213> ORGANISM: Artificial
<220> FEATURE:
<223> OTHER INFORMATION: Primer

<400> SEQUENCE: 5
ttccactttg gcataaggc                                                 19
```

USE OF URIDINE AND DEOXYURIDINE TO TREAT FOLATE-RESPONSIVE PATHOLOGIES

This application is a national stage application under 35 U.S.C. 371 of International Patent Application No. PCT/US2012/034963, filed Apr. 25, 2012, which claims the benefit of U.S. Provisional Patent Application Ser. No. 61/478,669, filed Apr. 25, 2011, and 61/515,356, filed Aug. 5, 2011, which are hereby incorporated by reference in their entirety.

This invention was made with government support under grant number HD059120 awarded by the National Institutes of Health-National Institute of Child Health and Human Development. The government has certain rights in this invention.

FIELD OF THE INVENTION

The present invention relates to compositions including deoxyuridine and methods of using the same. The present invention also relates to compositions comprising uridine and methods of using the same in treating and/or preventing cancer.

BACKGROUND OF THE INVENTION

Folate-mediated one-carbon metabolism is a metabolic network of interdependent biosynthetic pathways required for the de novo biosynthesis of purines, thymidylate ("dTMP"), and the remethylation of homocysteine to methionine (FIG. 1) (Barry Shane, *Folate Chemistry and Metabolism*, in FOLATE IN HEALTH AND DISEASE 1-22 (Lynn B. Bailey ed., Marcel Dekker, Inc. 1995)). Methionine can be converted to S-adenosylmethionine ("AdoMet"), the major one-carbon donor for cellular methylation reactions including the methylation of DNA, RNA, phospholipids, proteins, and small molecules (Barry Shane, *Folate Chemistry and Metabolism*, in FOLATE IN HEALTH AND DISEASE 1-22 (Lynn B. Bailey ed., Marcel Dekker, Inc. 1995); Fox et al., "Folate-Mediated One-Carbon Metabolism," *Vitam. Harm.* 79:1-44 (2008)). Impairments in one-carbon metabolism due to nutrient deficiencies and/or single nucleotide polymorphisms diminish dTMP synthesis, leading to elevated deoxyuridylate ("dUTP") pools, increased rates of dUTP misincorporation into DNA, and consequently futile cycles of DNA excision repair and chromosomal strand breaks (James et al., "Diet-Induced DNA Damage and Altered Nucleotide Metabolism in Lymphocytes from Methyl-Donor-Deficient Rats," *Carcinogenesis* 10(7):1209-1214 (1989); Branda et al., "Folate Deficiency Increases Genetic Damage Caused by Alkylating Agents and Gamma-Irradiation in Chinese Hamster Ovary Cells," *Cancer Res.* 53(22): 5401-5408 (1993); Duthie et al., "DNA Instability (Strand Breakage, Uracil Misincorporation, and Defective Repair) is Increased by Folic Acid Depletion in Human Lymphocytes in Vitro," *Faseb. J.* 12(14):1491-1497 (1998)).

Altered folate metabolism also influences chromatin methylation patterns, including genome-wide CpG hypomethylation and site-specific hypermethylation, and altered histone methylation, which modify gene expression patterns (Wainfan et al., "Methyl Groups in Carcinogenesis: Effects on DNA Methylation and Gene Expression," *Cancer Res.* 52(7 Suppl):2071s-2077s (1992); Friso et al., "A Common Mutation in the 5,10-Methylenetetrahydrofolate Reductase Gene Affects Genomic DNA Methylation Through an Interaction with Folate Status," *Proc. Natl. Acad. Sci. U.S.A.* 99(8):5606-5611 (2002); Gaudet et al., "Induction of Tumors in Mice by Genomic Hypomethylation," *Science* 300(5618):489-492 (2003)).

Therefore, the loss of DNA integrity due to increased genome instability and/or changes in gene expression due to altered genome methylation are candidate causal pathways for folate-mediated pathology. Population and clinical studies have established that impairment of folate-mediated one-carbon metabolism, due to nutritional deficiencies and/or variations in one-carbon metabolism genes increases risk for birth defects including neural tube defects ("NTDs"), chronic diseases including cardiovascular disease, and certain cancers. However, molecular mechanisms have not been established, and biomarkers that predict disease risk have not been established.

For instance, during embryogenesis, the neuroepithelium bends and fuses to form the embryonic neural tube through the process of neurulation. Failure of neurulation results in a spectrum of developmental anomalies collectively referred to as neural tube closure defects. Worldwide prevalence of human NTDs ranges from <1-30 per 10,000 births (INTERNATIONAL CLEARINGHOUSE FOR BIRTH DEFECTS MONITORING SYSTEMS, WORLD ATLAS OF BIRTH DEFECTS (World Health Organization, 2d ed. 2003)). One of the strongest environmental determinants of NTD risk is low maternal folate status (Kirke et al., "Maternal Plasma Folate and Vitamin B12 are Independent Risk Factors for Neural Tube Defects," *Q. J. Med.* 1993; 86:703-8 (1993)), which interacts with specific gene variants to confer NTD risk (Relton et al., "Low Erythrocyte Folate Status and Polymorphic Variation in Folate-Related Genes are Associated with Risk of Neural Tube Defect Pregnancy," *Mol. Genet. Metab.* 81:273-81 (2004); Christensen et al., "Genetic Polymorphisms in Methylenetetrahydrofolate Reductase and Methionine Synthase, Folate Levels in Red Blood Cells, and Risk of Neural Tube Defects," *Am. J. Med. Genet.* 84:151 7 (1999)).

Low maternal folate status is one of the strongest environmental determinants of neural tube defect risk (Kirke et al., "Maternal Plasma Folate and Vitamin B12 are Independent Risk Factors for Neural Tube Defects," *Q. J. Med.* 86(11):703-708 (1993)) and interacts with specific gene variants to confer NTD risk (Relton et al., "Low Erythrocyte Folate Status and Polymorphic Variation in Folate-Related Genes are Associated with Risk of Neural Tube Defect Pregnancy," *Mol. Genet. Metab.* 81(4):273-281 (2004); Christensen et al., "Genetic Polymorphisms in Methylenetetrahydrofolate Reductase and Methionine Synthase, Folate Levels in Red Blood Cells, and Risk of Neural Tube Defects," *Am. J. Med. Genet.* 84(2):151-157 (1999)). Periconceptional folic acid intake at a level of 400 µg per day is recommended to all women of childbearing age to reduce the occurrence of NTDs (CDC, "Recommendations for the Use of Folic Acid to Reduce the Number of Cases of Spina Bifida and Other Neural Tube Defects," *MMWR Recomm. Rep.* 41(1-7) (1992)). Furthermore, food folic acid fortification has been introduced in the US, Canada, and Chile (Honein et al., "Impact of Folic Acid Fortification of the US Food Supply on the Occurrence of Neural Tube Defects," *JAMA* 285(23):2981-2986 (2001)) and has significantly reduced rates of neural tube defects (Czeizel et al., "Prevention of the First Occurrence of Neural-Tube Defects by Periconceptional Vitamin Supplementation," *N. Engl. J. Med.* 327(26):1832-1835 (1992); Medical Research Council "Prevention of Neural Tube Defects: Results of the Medical Research Council Vitamin Study. MRC Vitamin Study Research Group," *Lancet* 338:131-7 (1991)). However, the folate-dependent metabolic pathway(s) that affect neural tube closure are unknown. It is estimated that only 70% of NTDs are responsive to dietary folic acid (Berry et al., "Prevention of Neural-Tube Defects with Folic Acid in China. China-U.S. Collaborative Project for Neural Tube Defect Prevention," *N. Engl. J. Med.* 341(20):1485-1490 (1999)). Other risk factors for NTD affected pregnancies include environmental and food-based toxins (Bhatt, "Environmental Influence on Reproductive Health," *Intl. J. Gynecology & Obstetrics* 70(1):69-75 (2000); Hutz et al., "Environmental Toxicants and Effects on Female Reproductive Function," *Trends Rep. Biol.* 2:1-11 (2006)), and obesity (Leddy et al., "The Impact of Maternal Obesity on Maternal and Fetal Health," *Rev. Obstetrics & Gynecology* 1(4):170-178 (2008)) and maternal diabetes (Hendricks et al., "Effects of Hyperinsulinemia and Obesity on Risk of Neural Tube Defects Among Mexican Americans," *Epidemiology* 12(6): 630-635 (2001)). It is not known what fraction of the 30% of NTDs that are not folic acid responsive result from impairments in folate-mediated one-carbon metabolism, including metabolic disruptions resulting from vitamin B12 deficiency. Although it has been appreciated that genetic variants interact with folate status to influence NTD risk (Wlodarczyk et al., "Spontaneous Neural Tube Defects in Splotch Mice Supplemented with Selected Micronutrients," *Toxicol. Appl. Pharmacol.* (2005)), the vast majority of the genetic risk has yet to be identified (Beaudin et al., "Insights into Metabolic Mechanisms Underlying Folate-Responsive Neural Tube Defects: A Minireview," *Birth Defects Res. A Clin. Mol. Teratol.* 85(4):274-284 (2009)).

As noted above, the causal metabolic pathways underlying folic acid-responsive NTDs have not been established. Further, folic acid supplementation has been linked to cancer prevalence (Ebbing et al., "Cancer Incidence and Mortality After Treatment With Folic Acid and Vitamin B12," *JAMA* 302(19): 2119-2126 (2009)). Thus, there is a great need for understanding the mechanisms underlying occurrence and recurrence of folate-deficiency related birth defects, as well as alternatives to folic acid supplementation.

The interactions among nutrients and genetic factors also play an important role in the development of numerous cancers including colorectal cancer ("CRC"). A strong, inverse association of folate status and CRC has been demonstrated; individuals with lowest dietary folate intake show a 40% to 60% increase in CRC risk when compared with individuals with highest folate intake (Giovannucci et al., "Folate, Methionine, and Alcohol intake and Risk of Colorectal Adenoma," *J. Natl. Cancer Inst.* 85:875-84 (1993); Ma et al., "Methylenetetrahydrofolate Reductase Polymorphism, Dietary Interactions, and Risk of Colorectal Cancer," *Cancer Res.* 57:1098-102 (1997); Kim et al., "Folate Intake and the Risk of Colorectal Cancer in a Korean Population," *Eur. J. Clin. Nutr.* 63:1057-64 (2009)). Genetic variation that alters folate metabolism and utilization also influences cancer risk (Ma et al., "Methylenetetrahydrofolate Reductase Polymorphism, Dietary Interactions, and Risk of Colorectal Cancer," *Cancer Res.* 57:1098-102 (1997)). The mechanism by which folate metabolism alters CRC risk is not known, which has led to concerns regarding the potential impact of elevated dietary folate intake and folate fortification initiatives on CRC incidence (Cole et al., "Folic Acid for the Prevention of Colorectal Adenomas: A Randomized Clinical Trial," *JAMA* 297:2351-9 (2007); Logan et al., "Aspirin and Folic Acid for the Prevention of Recurrent Colorectal Adenomas," *Gastroenterology* 134:29-38 (2008)).

The present invention is directed to overcoming these and other deficiencies in the art.

SUMMARY OF THE INVENTION

One aspect of the present invention relates to a pharmaceutical or dietary composition comprising deoxyuridine and a pharmaceutically or dietetically suitable carrier.

Another aspect of the present invention relates to a method of supplementing the dietary needs of a subject. This method includes administering to the subject a dietary supplementing effective amount of deoxyuridine.

Yet another aspect of the present invention relates to a method of treating cancer in a subject. This method includes selecting a subject having cancer and administering to the selected subject a therapeutically effective amount of uridine, thereby treating the cancer in the selected subject.

The present invention establishes that dietary uridine lowers tumor numbers in mice sensitized to intestinal tumors, feeding mouse dams dietary uridine during pregnancy increases risk for neural tube defects, and feeding mouse dams dietary deoxyuridine during pregnancy fully prevents neural tube defects. The Examples presented infra demonstrate that dietary uridine and deoxyuridine selectively prevent folate-associated pathologies.

Recently, it was established by the present inventor that reduced in SHMT1 expression in mice increases risk of colon cancer and birth defects in mice, indicating a key role for this gene in folate-related pathologies (Beaudin et al., "Shmt1 and de Novo Thymidylate Biosynthesis Underlie Folate-Responsive Neural Tube Defects in Mice," *Am. J. Clin. Nutr.* 93(4):789-798 (2011); MacFarlane et al., "Shmt1 Heterozygosity Impairs Folate-Dependent Thymidylate Synthesis Capacity and Modifies Risk of Apc$^{min}$-Mediated Intestinal Cancer Risk," *Cancer Res.* 71(6):2098-2107 (2011), which are hereby incorporated by reference in their entirety). These studies also implicate reduced capacity to synthesize thymidylate (dTMP) from uridylate (dUMP), which is the primary metabolic phenotype in Shmt$^{+/-}$ and Shmt$^{-/-}$ mice (MacFarlane et al., "Cytoplasmic Serine Hydroxymethyltransferase Regulates the Metabolic Partitioning of Methylenetetrahydrofolate But is Not Essential in Mice," *J. Biol. Chem.* 283(38):25846-25853 (2008), which is hereby incorporated by reference in its entirety), as a causal pathway in folate-associated birth defects, cancers, as well as other folate-responsive pathologies.

To better understand the causal mechanism for the role of SHMT in birth defects and cancer risk, experiments were conducted to rescue pathologies in Shmt1$^{+/-}$ and Shmt1$^{-/-}$ mice by providing metabolic intermediates in the diet. The present invention, supported by the Examples, infra, surprisingly establishes that treating mice with deoxyuridine (which is the substrate of the thymidylate cycle in which SHMT1 participates) prevents birth defects in Shmt1$^{+/-}$ and Shmt1$^{-/-}$ mice fed a folate-deficient diet, whereas uridine (which is the precursor for deoxyuridine biosynthesis) enhances birth defect rates in Shmt1$^{+/-}$ and Shmt1$^{-/-}$ pregnant mice fed either a folate-deficient or control diet. The increase in birth defects by dietary uridine was unexpected and indicates that dietary uridine caused birth defects in wild type embryos. The data surprisingly demonstrate that deoxyuridine prevents birth defects. Further, in a related study set forth in Examples 14 to 19, Apc-min mice (which are susceptible to intestinal tumors) were fed a diet containing supplemental uridine. It was surprisingly shown that mice fed the uridine exhibited approximately 50% fewer tumors. These discoveries are a significant advance in the prevention and treatment of folate-deficiency related pathologies.

BRIEF DESCRIPTION OF THE DRAWINGS

FIG. 1 is an illustration of folate-mediated one-carbon metabolism. Tetrahydrofolate ("THF")-mediated one-carbon metabolism is required for the synthesis of purines, thymidylate, and the remethylation of homocysteine to methionine. The hydroxymethyl group of serine is the major source of one-carbon units, which are generated in the mitochondria in the form of formate, or in the cytoplasm through the activity of SHMT1. Mitochondrial-derived formate can enter the cytoplasm and function as a one-carbon unit for folate metabolism. 5,10-methyleneTHF can be generated in the cytoplasm from formate or serine, and the sources of 5,10-methyleneTHF exist in equilibrium. The SHMT1 enzyme also inhibits homocysteine remethylation by sequestering 5-methylTHF in the cytoplasm. The thymidylate synthesis pathway involves the three enzymes, SHMT1, TYMS and DHFR. Abbreviations shown in the illustration are defined as follows: MTHFR, methylenetetrahydrofolate reductase; SHMT1, cytoplasmic serine hydroxymethyltransferase; DHFR, dihydrofolate reductase; TYMS, thymidylate synthase; MS, methionine synthase; AdoMet, S-adenosylmethionine; AdoHcy, S-adenosylhomocysteine; THF, tetrahydrofolate. The one-carbon is labeled in bold.

FIG. 2 is a table showing the details relating to experimental diets administered to mice.

FIG. 3 is a table showing experimental results. In particular, the number of implants, viable embryos, dead embryos and frequency of neural tube defects (NTDs) in Shmt1-deficient embryos on a 129/SvEv background as a function of maternal Shmt1 genotype and diet are shown. Values are means±SEM; n=10-13 litters for number of implants and viable embryos, dead embryos, and resorptions. Embryos for crown-rump (CR) length were considered only from litters uncovered at gestational day 11.5 for consistency. CR length was calculated as a function of maternal diet (n=24-64) and as a function of maternal diet and embryonic Shmt1 genotype (n=9-47). Differences between Genotypes, Diets, and interactions of Diet×genotype were analyzed by 2-factor ANOVA by using Tukey's honestly significant difference for post hoc analysis. Statistical analysis was compared to C group. Percentages are in parentheses. The legend for the Table shown in FIG. 3 is as follows: [1] Post hoc analysis did not show any significant comparison between number of dead embryos and implants when compared to C group. [2] Occurrence of resorptions were significantly different in FD and C+T diets from C diet according to Tukey's honestly significant difference for post hoc analysis. [3] Main effect of maternal Shmt1 genotype and maternal diet was assessed by using a modified generalized linear model procedure. Maternal diet significantly affected NTDs occurrence for Shmt1$^{-/-}$ genotype ($\chi^2$=43.565, P<0.0001); and did not affect in Shmt1$^{+/+}$ genotype (P=0.21 not significant (NS)). [4] Differences between groups were analyzed with Fisher's exact test of independence with Bonferroni's correction (n=8 for Diet or Genotype effect and n=16 for Diet×Genotype effect). All neural tube defects represent exencephaly and were assessed between gestational days 11.5-12.5. P=0.037 for the number of NTDs isolated from dams fed the FD diet compared with embryos isolated from dams fed the C diet. P=0.048 for the number of NTDs isolated from dams fed the U diet compared with embryos isolated from dams fed the C diet. P=0.0021 for the number of NTDs isolated from dams fed FD+U diet compared with embryos isolated from dams fed the C diet; P=0.042 for the number of NTDs isolated from Shmt1$^{-/-}$ dams fed FD+U diet compared with embryos isolated from Shmt1$^{-/-}$ dams fed the C diet; P=0.0133 for the number of NTDs isolated from dams fed FD+U diet compared with embryos isolated from dams fed the FD+dU diet. [5a] Embryos isolated form dams fed a C diet were significantly different from embryos from dams fed FD diet: ($\chi^2$=4.9669, P<0.0001). [5b] Embryos isolated form Shmt1$^{+/+}$ dams fed a C diet were significantly different from embryos from Shmt1$^{+/+}$ dams fed C+dU P<0.05 according to Tukeys honestly significant difference for post hoc analysis. a=1 NTD (Shmt1$^{-/+}$, M); b=5 NTDs (all Shmt1$^{-/+}$, 3 M, 2 F)+2 NTD found as dead embryos (2×Shmt1$^{-/-}$, F); c=4 NTDs (3×Shmt1$^{-/+}$, 1×Shmt1$^{+/+}$2 M, 2 F)+1 NTD found as dead embryo (Shmt1$^{-/+}$, F); d=3 (2×Shmt1$^{-/+}$, 1×Shmt1$^{-/-}$, 1 F, 2 M); e=3 NTDs (2×Shmt1$^{-/+}$, 1×Shmt1$^{+/+}$, 2 M, 1 F) and 1 NTD found as dead embryo (Shmt1$^{+/+}$, M); f=7 NTDs (3×Shmt1$^{-/+}$, 4×Shmt1$^{-/-}$, 5 F, 2 M) and 2 NTDs found as dead embryo (2×Shmt1$^{-/-}$, M and F); g=2 NTDs (1×Shmt1$^{+/+}$, Shmt1$^{-/+}$1 M, 1 F); h=3 NTDs (2×Shmt1$^{-/-}$, 1×Shmt1$^{-/+}$ 3M); F=female, M=male.

FIG. 4 is a table showing experimental results. In particular, results of frequency of NTDs in embryos as a function of maternal diet are shown.

FIG. 5 is a table showing metabolite levels of Shmt1$^{+/+}$ and Shmt1$^{-/-}$ females. These results show that Shmt1+/+ and Shmt1−/− mice exhibit altered plasma folate levels and blood glucose levels. The following were measured after administering the diet for 5 weeks: Uracil in liver DNA; Uridine, Thymidine, Deoxyuridine, and folates in plasma; and glucose in blood. The diets administered are as follows: AIN-93G as control (C); AIN-93G enriched with nucleotides (C+U; C+dU, C+T); and AIN-93G lacking folate (FD; FD+U, FD+dU; FD+T). Tissue values are represented as: fmol/uL for Folates; mg/dL for Glucose; pg/ug of DNA for Uracil; and uM for Uridine, Thymidine and Deoxyuridine. Values are expressed as mean±standard error (n=4-7).

DETAILED DESCRIPTION OF THE INVENTION

Figure 6:
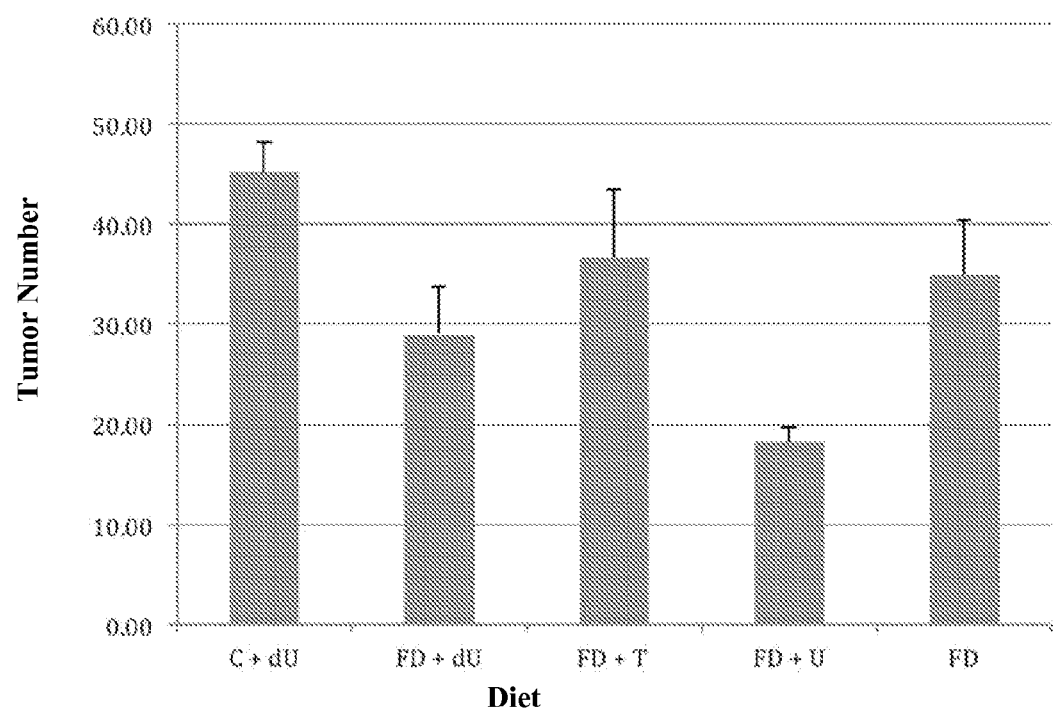
FIG. 6 is a bar graph summarizing results, which demonstrate that uridine supplementation treats intestinal tumors. Male Apc-min mice were fed either a AIN93G diet containing 0.1% deoxyuridine (C+dU); AIN93G lacking folic acid but containing 0.1% deoxyuridine (FD+dU); AIN93G lacking folic acid but containing 0.2% thymidine (FD+T); AIN93G lacking folic acid but containing 0.6% uridine (FD+U) or AIN93G lacking folic acid (FD). Mice fed the FD+U diet had nearly 50% fewer tumors than mice fed the FD diet (P=0.02).

As noted above, folates function as enzyme cofactors that carry and chemically activate one-carbons for a network of anabolic pathways collectively known as one-carbon metabolism ("OCM"). OCM is essential for de novo purine and thymidylate (dTMP) biosynthesis, and for the remethylation of homocysteine to methionine. Methionine can be adenosylated to form S-adenosylmethionine (AdoMet), a methyl donor for numerous cellular methylation reactions (FIG. 1). The inventor has developed the first model with a genetic disruption in the folate metabolism pathway that results in folic-acid responsive NTDs (Beaudin et al., "Shmt1 and De Novo Thymidylate Biosynthesis Underlie Folate-Responsive Neural Tube Defects in Mice," Am. J. Clin. Nutr. 93(4):789-798 (2011), which is hereby incorporated by reference in its entirety). This gene-diet interaction closely resembles the interactions found in human studies of NTD pathogenesis (Relton et al., "Low Erythrocyte Folate Status and Polymorphic Variation in Folate-Related Genes are Associated with Risk of Neural Tube Defect Pregnancy," *Mol. Genet. Metab.* 81(4):273-281 (2004); Christensen et al., "Genetic Polymorphisms in Methylenetetrahydrofolate Reductase and Methionine Synthase, Folate Levels in Red Blood Cells, and Risk of Neural Tube Defects," *Am. J. Med. Genet.* 84(2):151-157 (1999), which are hereby incorporated by reference in their entirety). Shmt1 is responsible for generating one-carbon units from the enzymatic cleavage of serine to glycine that are preferentially shunted to thymidylate biosynthesis. Shmt1$^{-/-}$ and Shmt1$^{+/-}$ mice are sensitized to folate-responsive NTDs, and demonstrate impaired de novo thymidylate biosynthesis, and therefore provide a means to study gene-nutrient interactions in NTDs (Beaudin et al., "Shmt1 and De Novo Thymidylate Biosynthesis Underlie Folate-Responsive Neural Tube Defects in Mice," *Am. J. Clin. Nutr.* 93(4):789-798 (2011), which is hereby incorporated by reference in its entirety).

Using this model, it was surprisingly discovered that deoxyuridine prevents folate-deficiency related birth defects and that uridine supplementation causes folate-deficiency related birth defects.

Accordingly, one aspect of the present invention relates to a pharmaceutical or dietary composition comprising deoxyuridine. In one embodiment, the composition includes a pharmaceutically or dietetically suitable carrier.

The compounds of the present invention may be provided as a composition with a pharmaceutically or dietetically acceptable carrier. Such dosage forms encompass physiologically acceptable carriers that are inherently non-toxic and non-therapeutic. Examples of such carriers include vegetable proteins, soy proteins, ion exchangers, soft gels, oils, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and PEG. Carriers for topical or gel-based forms include polysaccharides such as sodium carboxymethylcellulose or methylcellulose, polyvinylpyrrolidone, polyacrylates, polyoxyethylene-polyoxypropylene-block polymers, PEG, and wood wax alcohols. For all administrations, conventional depot forms are suitably used. Such forms include, for example, microcapsules, nano-capsules, liposomes, plasters, inhalation forms, nose sprays, sublingual tablets, and sustained-release preparations.

In accordance with the present invention, deoxyuridine or uridine (i.e., compounds according to the present invention), respectively, may be used to formulate pharmaceuticals, nutraceuticals, botanical drugs, herbal medicines, food additive, functional foods, medical foods, nutrition products, cosmetics, beverages, and the like.

Accordingly, in one embodiment of the present invention, the compound or composition is part of a nutraceutical composition, pharmaceutical composition, functional food, functional nutrition product, medical food, medical nutrition product, or dietary supplement.

In certain embodiments, compounds or compositions of the present invention may be combined with herbal medicines. In other embodiments, the compounds or compositions of the present invention may be formulated as botanical drugs. A botanical drug is a product that consists of vegetable materials, which may include plant materials, algae, macroscopic fungi, or combinations thereof, which is intended for use in the diagnosis, cure, mitigation, treatment, or prevention of disease in humans. In certain embodiments, the botanical drug product may be available as (but not limited to) a solution (e.g., tea), powder, tablet, capsule, elixir, topical, or injection.

In certain embodiments, compounds or compositions of the present invention may be formulated as nutraceuticals. Nutraceutical formulations of interest include foods for veterinary or human use, including health food bars, drinks and drink supplements, and the like. These foods are enhanced by the inclusion of a composition of the present invention. For example, in the treatment of an intestinal tumor, the normal diet of a patient may be supplemented by a nutraceutical formulation taken on a regular basis. Such nutraceuticals may or may not contain calories. The term nutraceutical composition as used herein include food product, foodstuff, dietary supplement, nutritional supplement or a supplement composition for a food product or a foodstuff. Thus, in another embodiment, the present invention relates to a nutraceutical wherein the nutraceutical is a food product, foodstuff, dietary supplement, nutritional supplement or a supplement composition for a food product or a foodstuff As used herein, the term food product refers to any food or feed suitable for consumption by humans or animals. The food product may be a prepared and packaged food (e.g., mayonnaise, salad dressing, bread, or cheese) or an animal feed (e.g., extruded and pelleted animal feed, coarse mixed feed or pet food composition). As used herein, the term foodstuff refers to any substance fit for human or animal consumption. Food products or foodstuffs are for example beverages such as non-alcoholic and alcoholic drinks as well as liquid preparation to be added to drinking water and liquid food, non-alcoholic drinks are for instance soft drinks, sport drinks, fruit juices, such as for example orange juice, apple juice and grapefruit juice; lemonades, teas, near-water drinks, milk, milk replacements, and other dairy drinks such as for example yoghurt drinks, and diet drinks. In another embodiment, food products or foodstuffs refer to solid or semi-solid foods comprising compounds or compositions of the present invention. These forms can include, but are not limited to baked goods such as bars, cakes, cookies, puddings, dairy products, confections, snack foods, or frozen confections or novelties (e.g., ice cream, milk shakes), prepared frozen meals, candy, snack products (e.g., chips), liquid food such as soups, spreads, sauces, salad dressings, prepared meat products, cheese, yogurt and any other fat or oil containing foods, and food ingredients (e.g., wheat flour). The term food products or foodstuffs also includes functional foods and prepared food products, the latter referring to any pre-packaged food approved for human consumption. The term functional food or functional nutrition product refers to a food or nutrition product that is sold (e.g., in a supermarket or online) without any restrictions. The term medical food or medical nutrition product refers to a food or nutrition product with is prescribed by a physician.

In certain embodiments, compounds or compositions of the present invention may be formulated as dietary supplements. Dietary supplements of the present invention may be delivered in any suitable format. In certain embodiments, dietary supplements are formulated for oral delivery. The ingredients of the dietary supplement of this invention are contained in acceptable excipients and/or carriers for oral consumption. The carrier may be a liquid, gel, gelcap, capsule, powder, solid tablet (coated or non-coated), tea, or the like. The dietary supplement is preferably in the form of a tablet or capsule. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). The various ingredients and the excipient and/or carrier are mixed and formed into the desired form using conventional techniques. The tablet or capsule of the present invention may be coated with an enteric coating that dissolves at a pH of about 6.0 to 7.0. A suitable enteric coating that dissolves in the small intestine but not in the stomach is cellulose acetate phthalate.

In other embodiments, the dietary supplement is provided as a powder or liquid suitable for adding by the consumer to a food or beverage. For example, in some embodiments, the dietary supplement can be administered to an individual in the form of a powder, for instance to be used by mixing into a beverage, or by stirring into a semi-solid food such as a pudding, topping, sauce, puree, cooked cereal, or salad dressing, for instance, or by otherwise adding to a food (e.g., enclosed in caps of food or beverage containers for release immediately before consumption).

The dietary supplement may comprise one or more inert ingredients, especially if it is desirable to limit the number of calories added to the diet by the dietary supplement. For example, the dietary supplement of the present invention may also contain optional ingredients including, for example, herbs, vitamins, minerals, enhancers, colorants, sweeteners, flavorants, inert ingredients, and the like.

In other embodiments, the present invention provides nutritional supplements (e.g., energy bars or meal replacement bars or beverages) comprising compounds or compositions of the present invention. The nutritional supplement may serve as meal or snack replacement and generally provide nutrient calories. However, as noted above, supplements which do not contain calories may also be used. In certain embodiments, the nutritional supplements provide carbohydrates, proteins, and fats in balanced amounts. The nutritional supplement can further comprise carbohydrate, simple, medium chain length, or polysaccharides, or a combination thereof. A simple sugar can be chosen for desirable organoleptic properties. Uncooked cornstarch is one example of a complex carbohydrate. If it is desired that it should maintain its high molecular weight structure, it should be included only in food formulations or portions thereof which are not cooked or heat processed since the heat will break down the complex carbohydrate into simple carbohydrates, wherein simple carbohydrates are mono- or disaccharides. The nutritional supplement contains, in one embodiment, combinations of sources of carbohydrate of three levels of chain length (simple, medium and complex (e.g., sucrose, maltodextrins, and uncooked cornstarch)).

Sources of protein to be incorporated into the nutritional supplement of the invention can be any suitable protein utilized in nutritional formulations and can include whey protein, whey protein concentrate, whey powder, egg, soy flour, soy milk soy protein, soy protein isolate, caseinate (e.g., sodium caseinate, sodium calcium caseinate, calcium caseinate, potassium caseinate), animal and vegetable protein and hydrolysates or mixtures thereof. Soy protein have an almost perfect PDCAA, Protein Digestibility Corrected Amino Acid Score (PDCAAS) and by this criterion soy protein is the nutritional equivalent of meat and eggs for human growth and health. These proteins have high biological value (i.e., a high proportion of the essential amino acids). See MODERN NUTRITION IN HEALTH AND DISEASE (Lea & Febiger, 8th ed. 1986), which is hereby incorporated by reference in its entirety.

The nutritional supplement can also contain other ingredients, such as one or a combination of other vitamins, minerals, antioxidants, fiber and other dietary supplements (e.g., protein, amino acids, choline, lecithin, omega-3 fatty acids, and others discussed herein). Selection of one or several of these ingredients is a matter of formulation, design, consumer preference and end-user. The amounts of these ingredients added to the dietary supplements of this invention are readily known to the skilled artisan. In one embodiment, vitamins and/or minerals are added, as described below.

The nutritional supplement can be provided in a variety of forms, and by a variety of production methods. In one embodiment, to manufacture a food bar, the liquid ingredients are cooked; the dry ingredients are added with the liquid ingredients in a mixer and mixed until the dough phase is reached; the dough is put into an extruder, and extruded; the extruded dough is cut into appropriate lengths; and the product is cooled. The bars may contain other nutrients and fillers to enhance taste, in addition to the ingredients specifically listed herein.

As is understood by those of skill in the art, other ingredients can be added to those described herein, for example, fillers, emulsifiers, preservatives, for the processing or manufacture of a nutritional supplement.

Additionally, flavors, coloring agents, spices, nuts and the like may be incorporated into the formulations described herein. Flavorings can be in the form of flavored extracts, volatile oils, chocolate flavorings, peanut butter flavoring, cookie crumbs, crisp rice, vanilla or any commercially available flavoring. Examples of useful flavoring include, but are not limited to, pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, walnut oil, cherry oil, cinnamon oil, clove oil, or peppermint oil.

Emulsifiers may be added for stability of the formulations. Examples of suitable emulsifiers include, but are not limited to, lecithin (e.g., from egg or soy), and/or mono- and di-glycerides. Other emulsifiers are readily apparent to the skilled artisan and selection of suitable emulsifier(s) will depend, in part, upon the formulation and final product. Preservatives may also be added to the formulations to extend product shelf life. For example, preservatives such as potassium sorbate, sodium sorbate, potassium benzoate, sodium benzoate or calcium disodium EDTA are used.

In addition to the carbohydrates described above, the formulations can contain natural or artificial (preferably low calorie) sweeteners, e.g., saccharides, cyclamates, aspartamine, aspartame, acesulfame K, and/or sorbitol. Such artificial sweeteners can be desirable if the nutritional supplement is intended to be consumed by an overweight or obese individual, or an individual with type II diabetes who is prone to hyperglycemia.

Moreover, a multi-vitamin and mineral supplement may be added to the formulations or compositions of the present invention to obtain an adequate amount of an essential nutrient, which is missing in some diets. The multi-vitamin and mineral supplement may also be useful for disease prevention and protection against nutritional losses and deficiencies due to lifestyle patterns.

In accordance with the present invention, compounds or compositions of the present invention may be prepared as pharmaceutical compositions, such as those which may be particularly useful for the treatment or prevention of folate-deficiency related diseases (e.g., folate-deficiency related birth defects) and cancer (e.g., intestinal tumors), respectively. Such compositions comprise a compound of the present invention (e.g., deoxyuridine and/or uridine) or a pharmaceutically acceptable salt, biologically active metabolite, solvate, hydrate, prodrug, enantiomer or stereoisomer thereof, and a pharmaceutically acceptable carrier and/or excipient.

The compositions of the present invention may be administered by various means, depending on their intended use, as is well known in the art. For example, if compositions of the present invention are to be administered orally, they may be formulated as tablets, capsules, granules, powders or syrups. Alternatively, formulations of the present invention may be administered parenterally as injections (intravenous, intramuscular, or subcutaneous), drop infusion preparations or suppositories. For application by the ophthalmic mucous membrane route, compositions of the present invention may be formulated as eye drops or eye ointments. These formulations may be prepared by conventional means, and, if desired, the compositions may be mixed with any conventional additive, such as an excipient, a binder, a disintegrating agent, a lubricant, a corrigent, a solubilizing agent, a suspension aid, an emulsifying agent or a coating agent.

In formulations of the subject invention, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

In one embodiment, the compound or composition according to the present invention is administered parenterally. In another embodiment of the present invention, the compound or composition according to the present invention is administered orally.

In one embodiment, the compound or composition according to the present invention is in capsule, tablet, granule, or lozenge form.

Subject formulations may be suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of composition that may be combined with a carrier material to produce a single dose vary depending upon the subject being treated, and the particular mode of administration.

Methods of preparing these formulations include the step of bringing into association compositions of the present invention with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the present invention may also be administered as a bolus, electuary, or paste.

In solid dosage forms for oral administration (capsules, tablets, pills, dragees, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using excipients such as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as dragees, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent. Formulations which are suitable for vaginal administration also include pessaries, tampons, creams, gels, pastes, foams or spray formulations containing such carriers as are known in the art to be appropriate.

Dosage forms for transdermal administration of a subject composition includes powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions.

Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics®, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity may be maintained, for example, by the use of coating materials, such as lecithin, by the maintenance of the required particle size in the case of dispersions, and by the use of surfactants.

In certain embodiments, the compositions are formulated as a tablet, pill capsule, or other appropriate ingestible formulation, to provide a therapeutic dose in 10 ingestible formulations or fewer. In another example, a therapeutic dose is provided in 20, 15, 10, 5, 4, 3, or 2 ingestible formulations.

The compositions of the present invention may be in the form of a dispersible dry powder for pulmonary delivery.

Dry powder compositions may be prepared by processes known in the art, such as lyophilization and jet milling, as disclosed in WO 91/16038 and as disclosed in U.S. Pat. No. 6,921,527, which are hereby incorporated by reference in their entirety. The composition of the present invention may be placed within a suitable dosage receptacle in an amount sufficient to provide a subject with a unit dosage treatment. The dosage receptacle may be one that fits within a suitable inhalation device to allow for the aerosolization of the dry powder composition by dispersion into a gas stream to form an aerosol and then capturing the aerosol so produced in a chamber having a mouthpiece attached for subsequent inhalation by a subject in need of treatment. Such a dosage receptacle includes any container enclosing the composition known in the art such as gelatin or plastic capsules with a removable portion that allows a stream of gas (e.g., air) to be directed into the container to disperse the dry powder composition. Such containers are exemplified by those shown in U.S. Pat. No. 4,227,522; U.S. Pat. No. 4,192,309; and U.S. Pat. No. 4,105,027, which are hereby incorporated by reference in their entirety.

A transdermal delivery system, transdermal patch, or patch refer to an adhesive system placed on the skin to deliver a time released dose of a drug(s) by passage from the dosage form through the skin to be available for distribution via the systemic circulation. Transdermal patches are a well-accepted technology used to deliver a wide variety of pharmaceuticals, including, but not limited to, scopolamine for motion sickness, nitroglycerin for treatment of angina pectoris, clonidine for hypertension, estradiol for postmenopausal indications, and nicotine for smoking cessation. Patches suitable for use in the present invention include, but are not limited to, (1) the matrix patch; (2) the reservoir patch; (3) the multi-laminate drug-in-adhesive patch; and (4) the monolithic drug-in-adhesive patch (TRANSDERMAL AND TOPICAL DRUG DELIVER SYSTEMS (Ghosh et al. eds., 1997), which is hereby incorporated by reference in its entirety). These patches are well known in the art and generally available commercially.

The compositions of the present inventive subject matter may optionally contain folic acid, as well as any other vitamins, minerals, nutritional agents, therapeutic agents and the like. In one embodiment, the pharmaceutical or dietary composition includes one or more vitamins, one or more minerals, or combinations thereof.

These vitamins, minerals and trace elements include, for example, Vitamin A or beta-carotene, Vitamin B1 (as Thiamin or Thiamin mononitrate), Vitamin B2 (as Riboflavin), Vitamin B3 (as Niacin), Vitamin B6 (as Pyridoxine or Pyridoxine hydrochloride), Vitamin B9 (Folic Acid), Vitamin B12 (cyanocobalamine), Vitamin H (Biotin), Vitamin C (Ascorbic Acid), Vitamin D, Vitamin E (as d1-Alpha Tocopherol Acetate), Vitamin K, Folacin, Niacinamide, Iron (as Ferrous Fumarate), Phosphorus, Pantothenic Acid (as Calcium Pantothenate), Iodine (as Potassium Iodide), Magnesium (as Magnesium Oxide), Zinc (as Zinc Oxide), Selenium (as Sodium Selenate), Copper (as Cupric Oxide), Manganese (as Manganese Sulfate), Chromium (as Chromium Chloride), Molybdenum (as Sodium Molybdate), Choline, Fluoride, Chloride, Potassium, Sodium, and mixtures thereof. Such vitamins, minerals and trace elements are commercially available from sources known by those of skill in the art. The dosage forms of the invention may be formulated using any pharmaceutically-acceptable forms of the vitamins and/or minerals described above, including their salts, which are known by those of skill in the art.

In one embodiment, the pharmaceutical or dietary composition according to the present invention includes one or more vitamins, minerals, trace elements, or combinations thereof selected from the group consisting of Vitamin A, Vitamin C, Vitamin D, Vitamin E, Vitamin K, Thiamin, Riboflavin, Niacin, Folate, Vitamin B12, Vitamin B6, Pantothenic Acid, Biotin, Choline, Chromium, Copper, Iodine, Molybdenum, Selenium, Iron, Zinc, Magnesium, and combinations thereof.

As noted above, compositions according to the present invention may also include folate or derivatives thereof. Folate derivatives include folic acid and derivatives thereof. Derivatives of folic acid include compounds formed from folic acid which may be structurally distinct from folic acid, but which retain the active function of folic acid. Non-limiting examples of such derivatives include salts of folic acid, alkaline salts of folic acid, esters of folic acid, chelates of folic acid and combinations thereof.

The folate or derivatives thereof may be present in an amount, for example, ranging from about 0.01 mg to about 5 mg. In certain embodiments, the compositions according to the present invention includes less than about 1000 μg, less than about 400 μg, less than about 300 μg, less than about 200 μg, or less than about 100 μg of folate or derivatives thereof.

In one embodiment according to the present invention, the composition comprises folate or derivatives thereof where the amount of folate or derivatives thereof present is the daily recommended dietary allowance for a particular subject (e.g., woman of childbearing years). As will be appreciated, the daily recommended dietary allowance for particular nutrients is published by the National Academies Press (See National Academy of Sciences, Institute of Medicine, Food and Nutrition Board, "Dietary Reference Intakes (DRIs): Recommended Dietary Allowances and Adequate Intakes," (2011), which is hereby incorporated by reference in its entirety). In an other embodiment, the amount of folic acid in the composition is an amount that is less than the daily recommended dietary allowance of folate or derivatives thereof for a particular subject (e.g., woman of childbearing years, pregnant woman, or lactating woman). In certain embodiments, the amount of folate or derivatives thereof is at least about 25%, 30%, 35%, 40%, 45%, 50%, 55%, 60%, 65%, 70%, 75%, 80%, 85%, 90%, 95%, or 100% less than that recommended as a daily dietary allowance for a particular individual (e.g., a woman of childbearing age).

In another embodiment of the present invention, the composition comprises deoxyuridine and other vitamins, with the proviso that the vitamins do not include folic acid.

Effective doses of the compounds (e.g., deoxyuridine and/or uridine) of the present invention vary depending upon many different factors, including type and stage of disease, mode of administration, target site, physiological state of the patient, other medications or therapies administered, and physical state of the patient relative to other medical complications. Treatment dosages need to be titrated to optimize safety and efficacy.

The compositions of the present invention can be administered in a single dose or multiple doses. The dosage can be determined by methods known in the art and can be dependent, for example, upon the individual's age, sensitivity, tolerance and overall well-being.

The dosage forms of the present invention may involve the administration of a composition according to the present invention in a single dose during a 24 hour period of time, a double dose during a 24 hour period of time, or more than two doses during a 24 hour period of time, or fractional doses to be taken during a 24 hour period of time. The double or multiple doses may be taken simultaneously or at different times during the 24 hour period.

It is also contemplated that the compositions according to the present invention are formulated for the dosage form to combine various forms of release, which include, without limitation, immediate release, extended release, pulse release, variable release, controlled release, timed release, sustained release, delayed release, long acting, and combinations thereof. The ability to obtain immediate release, extended release, pulse release, variable release, controlled release, timed release, sustained release, delayed release, long acting characteristics and combinations thereof is performed using well known procedures and techniques available to the ordinary artisan.

In one embodiment, the dose in a range from about 0.5 mg/kg body weight per day to about 200 mg/kg body weight per day. In another embodiment, the dose is in a range from about 0.5 mg/kg body weight per day to about 150 mg/kg body weight per day. In another embodiment, the dose is in a range from about 0.5 mg/kg body weight per day to about 100 mg/kg body weight per day. In another embodiment, the dose is in a range from about 0.5 mg/kg body weight per day to about 95 mg/kg body weight per day. In another embodiment, the dose is in a range from about 0.5 mg/kg body weight per day to about 90 mg/kg body weight per day. In another embodiment, the dose is in a range from about 0.5 mg/kg body weight per day to about 85 mg/kg body weight per day. In another embodiment, the dose is in a range from about 0.5 mg/kg body weight per day to about 80 mg/kg body weight per day. In another embodiment, the dose is in a range from about 0.5 mg/kg body weight per day to about 75 mg/kg body weight per day. In another embodiment, the dose is in a range from about 0.5 mg/kg body weight per day to about 70 mg/kg body weight per day. In another embodiment, the dose is in a range from about 0.5 mg/kg body weight per day to about 65 mg/kg body weight per day. In another embodiment, the dose is in a range from about 0.5 mg/kg body weight per day to about 60 mg/kg body weight per day. In another embodiment, the dose is in a range from about 0.5 mg/kg body weight per day to about 55 mg/kg body weight per day. In another embodiment, the dose is in a range from about 0.5 mg/kg body weight per day to about 50 mg/kg body weight per day. In another embodiment, the dose is in a range from about 0.5 mg/kg body weight per day to about 45 mg/kg body weight per day. In another embodiment, the dose is in a range from about 0.5 mg/kg body weight per day to about 40 mg/kg body weight per day. In another embodiment, the dose is in a range from about 0.5 mg/kg body weight per day to about 35 mg/kg body weight per day. In another embodiment, the dose is in a range from about 0.5 mg/kg body weight per day to about 30 mg/kg body weight per day. In another embodiment, the dose is in a range from about 0.5 mg/kg body weight per day to about 25 mg/kg body weight per day. In another embodiment, the dose is in a range from about 0.5 mg/kg body weight per day to about 20 mg/kg body weight per day. In another embodiment, the dose is in a range from about 0.5 mg/kg body weight per day to about 15 mg/kg body weight per day. In another embodiment, the dose is in a range from about 0.5 mg/kg body weight per day to about 10 mg/kg body weight per day. In another embodiment, the dose is in a range from about 0.5 mg/kg body weight per day to about 5 mg/kg body weight per day. In another embodiment, the dose is in a range from about 0.5 mg/kg body weight per day to about 4 mg/kg body weight per day. In another embodiment, the dose is in a range from about 0.5 mg/kg body weight per day to about 3 mg/kg body weight per day. In another embodiment, the dose is in a range from about 0.5 mg/kg body weight per day to about 2 mg/kg body weight per day. In another embodiment, the dose is in a range from about 0.5 mg/kg body weight per day to about 1 mg/kg body weight per day.

In certain embodiments, the dose is or is at least about 0.1, 0.2, 0.3, 0.4, 0.5, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 125, 150, 175, or 200 mg/kg body weight per day.

In certain embodiments, the therapeutic dose may be between about 10 mg/day and 15,000 mg/day, between about 100 mg/day and 2,500 mg/day, or between 250 mg to about 1,000 mg/day. In other embodiments, other ranges may be used, including, for example, 50-250 mg/day, 250-500 mg/day, and 500-750 mg/day. The amount of the compound required for prophylactic treatment, referred to as a prophylactically-effective dosage, is generally the same as described for effective dose.

In certain embodiments, the effective dose is between about 50 mg/day to about 150 mg/day. In certain embodiments, the therapeutic dose is between about 10 mg/day and about 20 mg/day. In certain embodiments, the therapeutic dose is between about 20 mg/day and about 30 mg/day. In certain embodiments, the therapeutic dose is between about 30 mg/day and about 40 mg/day. In certain embodiments, the therapeutic dose is between about 40 mg/day and about 50 mg/day. In certain embodiments, the therapeutic dose is between about 50 mg/day and about 60 mg/day. In certain embodiments, the therapeutic dose is between about 60 mg/day and about 70 mg/day. In certain embodiments, the therapeutic dose is between about 70 mg/day and about 80 mg/day. In certain embodiments, the therapeutic dose is between about 80 mg/day and about 90 mg/day. In certain embodiments, the therapeutic dose is between about 90 mg/day and about 100 mg/day. In certain embodiments, the therapeutic dose is between about 100 mg/day and about 110 mg/day. In certain embodiments, the therapeutic dose is between about 110 mg/day and about 120 mg/day. In certain embodiments, the therapeutic dose is between about 120 mg/day and about 130 mg/day. In certain embodiments, the therapeutic dose is between about 130 mg/day and about 140 mg/day. In certain embodiments, the therapeutic dose is between about 140 mg/day and about 150 mg/day. In certain embodiments, the therapeutic dose is between about 150 mg/day and about 160 mg/day. In certain embodiments, the therapeutic dose is between about 160 mg/day and about 170 mg/day. In certain embodiments, the therapeutic dose is between about 170 mg/day and about 180 mg/day. In certain embodiments, the therapeutic dose is between about 180 mg/day and about 190 mg/day. In certain embodiments, the therapeutic dose is between about 190 mg/day and about 200 mg/day. In certain embodiments, the therapeutic dose is between about 200 mg/day and about 250 mg/day. In certain embodiments, the therapeutic dose is between about 250 mg/day and about 300 mg/day. In certain embodiments, the therapeutic dose is between about 300 mg/day and about 350 mg/day. In certain embodiments, the therapeutic dose is between about 350 mg/day and about 400 mg/day. In certain embodiments, the therapeutic dose is between about 400 mg/day and about 450 mg/day. In certain embodiments, the therapeutic dose is between about 450 mg/day and about 500 mg/day. In certain embodiments, the therapeutic dose is between about 500 mg/day and about 550 mg/day. In certain embodiments, the therapeutic dose is between about 550 mg/day and about 600 mg/day. In certain embodiments, the therapeutic dose is between about 600 mg/day and about 650 mg/day. In certain embodiments, the therapeutic dose is between about 650 mg/day and about 700 mg/day. In certain embodiments, the therapeutic dose is between about 700 mg/day and about 750 mg/day. In certain embodiments, the therapeutic dose is between about 750 mg/day and about 800 mg/day. In certain embodiments, the therapeutic dose is between about 800 mg/day and about 850 mg/day. In certain embodiments, the therapeutic dose is between about 850 mg/day and about 900 mg/day. In certain embodiments, the therapeutic dose is between about 900 mg/day and about 950 mg/day. In certain embodiments, the therapeutic dose is between about 950 mg/day and about 1000 mg/day. In certain embodiments, the therapeutic dose is between about 1000 mg/day and about 1050 mg/day. In certain embodiments, the therapeutic dose is between about 1050 mg/day and about 1100 mg/day. In certain embodiments, the therapeutic dose is between about 1100 mg/day and about 1150 mg/day. In certain embodiments, the therapeutic dose is between about 1150 mg/day and about 1200 mg/day. In certain embodiments, the therapeutic dose is between about 1200 mg/day and about 1250 mg/day. In certain embodiments, the therapeutic dose is between about 1250 mg/day and about 1300 mg/day. In certain embodiments, the therapeutic dose is between about 1300 mg/day and about 1350 mg/day. In certain embodiments, the therapeutic dose is between about 1350 mg/day and about 1400 mg/day. In certain embodiments, the therapeutic dose is between about 1400 mg/day and about 1450 mg/day. In certain embodiments, the therapeutic dose is between about 1450 mg/day and about 1500 mg/day.

An effective dose or amount, and any possible affects on the timing of administration of the formulation, may need to be identified for any particular composition of the present invention. This may be accomplished by routine experiment, using one or more groups of animals, or in human trials if appropriate. The effectiveness of any subject composition and method of treating may be assessed by administering the composition and assessing the effect of the administration by measuring one or more applicable indices, and comparing the post-treatment values of these indices to the values of the same indices prior to treatment.

Another aspect of the present invention relates to a method of supplementing the dietary needs of a subject. This method includes administering to the subject a dietary supplementing effective amount of deoxyuridine. Suitable compositions, dosages, formulations, modes of administration, etc., are described above.

In one embodiment, the subject of methods of the present invention is a mammal. In another embodiment, the subject is a human. In another embodiment, the subject is a rodent. In another embodiment, the subject is a laboratory animal. In another embodiment, the subject is a male. In another embodiment, the subject is a female. In another embodiment, the subject is any other type of subject known in the art.

In one embodiment, the subject is a pregnant woman, lactating woman, or woman of childbearing age.

In this embodiment of the present invention, administering deoxyuridine to the subject prevents development of, or reduces the risk for developing, folate-deficiency related birth defects. One class of folate-deficiency related birth defects is neural tube defects. Neural tube defects include, but are not limited to, anencephaly, encephaloceles, hydranencephaly, iniencephaly, schizencephaly, spina bifida, lipomyelomeningocele, lipomeningocele, and tethered cord.

In one embodiment, the woman is a woman of childbearing age that is attempting to become pregnant. A woman of childbearing age that is attempting to become pregnant includes, for example, women using assisted reproductive technology (e.g., in vitro fertilization (IVF)), women monitoring fertility, and women generally attempting to conceive a child. In one embodiment, deoxyuridine or a composition comprising deoxyuridine is administered in conjunction with a fertility agent (e.g., FSH, GnRh, Clomiphene citrate, or HMG).

In another embodiment, the subject is a woman who is at risk for developing a fetus with folate-deficiency related birth defects. This includes, for example, a woman who is predisposed to for developing a fetus with folate-deficiency related birth defects. For example, a woman may be at risk for developing a fetus with folate-deficiency related birth defects due to low consumption of folate, obesity, and/or diabetes. This also includes, for example, a woman who has developed a fetus with folate-deficiency related birth defects in the past.

Further, as described in more detail with respect to the Examples below, uridine is shown to increase the incidence of folate-deficiency related birth defects. Accordingly, in one embodiment, the method further includes decreasing the level of uridine in the diet of the subject. For example, this includes reducing the amount of uridine consumed by the subject. This includes, for example, eliminating dietary sources of uridine (e.g., tomatoes, beer, broccoli, and organ meats, as well as supplements, drugs, or other sources of uridine.).

Kits (e.g., fertility kits) including compounds and compositions according to the present invention are also contemplated. In one embodiment, the kit includes one or more doses of deoxyuridine or a composition comprising deoxyuridine according to the present invention, an ovulation monitoring component, and a set of instructions for timing and utilization of the compounds and/or compositions according to the present invention together with timing intercourse to maximize fertility potential. The monitoring component may include, for example, a monitor of salivary electrolytes, basal body temperature, or luteinizing hormone (LH), to predict and determine when ovulation will/has occurred. In one embodiment, the ovulation monitoring component includes a basal body temperature chart for cataloging the typical menstrual cycle for the female.

Yet another aspect of the present invention relates to a method of treating and/or preventing cancer in a subject. In one embodiment, the method is a method for treating cancer in a subject. This method includes selecting a subject having cancer and administering to the selected subject a therapeutically effective amount of uridine, thereby treating the cancer in the selected subject.

Cancer treated according to this aspect of the present invention includes intestinal tumors. In one embodiment, the cancer is colorectal cancer. In one embodiment, the cancer is a tumor in the colon.

As used herein, treating refers to a reduction in cancer disease state or condition as compared to the disease state or condition without or before administering the compound or composition according to the present invention. Such treatment can be, but is not limited to, the complete ablation of the disease, condition, or the symptoms of the disease or condition. For example, a disclosed method for treating cancer is considered to be a treatment if there is a reduction in one or more symptoms of the disease (e.g., tumor size) in a subject with the disease when compared to native levels in the same subject or control subjects. Thus, the reduction can be a 5, 10, 20, 30, 40, 50, 60, 70, 80, 90, 100%, or any amount of reduction in between as compared to native or control levels. It is also understood and contemplated herein that treatment can refer to any reduction in the progression of a disease or cancer. Thus, for example, methods of reducing the effects of a cancer is considered to be a treatment if there is a reduction in the tumor growth rate relative to a control subject or tumor growth rates in the same subject prior to the treatment. It is understood that the reduction can be a 5, 10, 20, 30, 40, 50, 60, 70, 80, 90, 100%, or any amount of reduction in between as compared to native or control levels.

In another embodiment, the method according to this aspect of the invention is a method of preventing cancer in a subject. The method includes selecting a subject at risk for developing cancer and administering to the selected subject a therapeutically effective amount of uridine, thereby preventing cancer in the selected subject. Types of cancer preventable according to this aspect of the present invention are described above.

Those at risk for developing intestinal cancer include, for example, subjects having one or more risk factors for developing intestinal cancer. Risk factors for developing intestinal cancers include, for example, a personal history of colorectal cancer or polyps; inflammatory intestinal conditions (e.g., Chronic inflammatory diseases of the colon, such as ulcerative colitis and Crohn's disease); inherited syndromes that increase cancer risk (genetic syndromes such as familial adenomatous polyposis and hereditary nonpolyposis colorectal cancer); family history of intestinal cancers (e.g., colon cancer and colon polyps); diabetes; obesity; smoking; heavy use of alcohol; and radiation therapy for cancer.

In one embodiment, the subject of methods of the present invention is a mammal. In another embodiment, the subject is a human. In another embodiment, the subject is a rodent. In another embodiment, the subject is a laboratory animal. In another embodiment, the subject is a male. In another embodiment, the subject is a female. In another embodiment, the subject is any other type of subject known in the art. In one embodiment in accordance with this aspect of the present invention, the selected subject is not a woman of childbearing age. In one embodiment, the subject is not a woman of childbearing age who is attempting to become pregnant.

In accordance with this aspect of the present invention, uridine includes uridine, an acyl derivative thereof, or a uridine phosphate. In one embodiment, uridine phosphate is a uridine-5'-monophosphate (UMP), uridine-5'-diphosphate (UDP), uridine-5'-triphosphate (UTP), or is a salt of said UMP, UDP, or UTP.

Uridine administered to the selected subject in accordance with this aspect of the present invention may be formulated as a composition in the manner described above. In particular, suitable compositions, formulations, dosages, modes of administration, etc., that include or relate to compounds according to the present invention (e.g., deoxyuridine, uridine, and/or derivatives thereof) are described above. Other pharmaceutical and dietary compositions including uridine are known and may also be used in accordance with the methods of the present invention (e.g., U.S. Patent Application Publication Nos. 2009/0105189 to Wurtman et al. and 2010/0222296 to Renshaw, which are hereby incorporated by reference in their entirety).

In one embodiment, one or more vitamins, minerals, trace elements, or combinations thereof are also administered. The one or more vitamins, minerals, trace elements, or combinations thereof can be selected from the group consisting of Vitamin A, Vitamin C, Vitamin D, Vitamin E, Vitamin K, Thiamin, Riboflavin, Niacin, Folate, Vitamin B12, Vitamin B6, Pantothenic Acid, Biotin, Choline, Chromium, Copper, Iodine, Molybdenum, Selenium, Iron, Zinc, Magnesium, and combinations thereof.

In one embodiment, the uridine is administered as part of a composition selected from the group consisting of a nutraceutical composition, pharmaceutical composition, functional food, functional nutrition product, medical food, medical nutrition product, or dietary supplement.

In one embodiment, the administering is parenteral. In another embodiment, the administering is oral. In one embodiment, the uridine is administered in capsule, tablet, granule, or lozenge form.

Administering uridine according to the present invention can be used alone or in conjunction with other cancer therapies (e.g., chemotherapeutic agents, radiation, surgery, or combinations thereof). Accordingly, in one embodiment, a therapeutically effective amount of uridine is administered in conjunction with a cancer therapy.

In one embodiment, the cancer therapy is a chemotherapeutic. In one embodiment, the chemotherapeutic is selected from the group consisting of alkylating agents, antimetabolites, anthracyclines, antitumor antibiotics, platinum-based chemotherapeutics, and plant alkaloids.

Particular examples of chemotherapeutics or chemotherapy include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin, paclitaxel (taxol), docetaxel (taxotere), aldesleukin, asparaginase, busulfan, carboplatin, cladribine, dacarbazine, floxuridine, fludarabine, hydroxyurea, ifosfamide, interferon alpha, leuprolide, magastrol, melphalan, mercaptopurine, oxaloplatin, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil, taxol, and combinations thereof.

In one embodiment, the cancer therapy is radiation. The source of radiation can be either external or internal to the patient being treated. When the source is external to the patient, the therapy is known as external beam radiation therapy (EBRT). When the source of radiation is internal to the patient, the treatment is called brachytherapy (BT).

In another embodiment, the cancer therapy is surgery.

In one embodiment, the therapeutically effective amount of uridine and the cancer therapy are administered simultaneously. In another embodiment, the therapeutically effective amount of uridine is administered prior to the cancer therapy. In yet another embodiment, the therapeutically effective amount of uridine is administered following the cancer therapy.

EXAMPLES

The following examples are provided to illustrate embodiments of the present invention but are by no means intended to limit its scope.

Example 1

Mouse Model

NTDs were examined in litters harvested from crosses of 129SvEv-Shmt1 (N=10 and more) mice. Shmt1$^{+/-}$, Shm1$^{+/+}$, and Shmt1$^{-/-}$ mice were generated from Shmt1$^{+/-}$ breeding pairs maintained as a heterozygote breeding colonies. Shmt1$^{+/+}$ and Shmt1$^{-/-}$ female mice were then crossed to Shmt1$^{+/-}$ male mice for timed mating experiments, as described below.

Example 2

Experimental Animals and Diets

Mice were maintained on a 12-hour light/dark cycle in a temperature-controlled room. For studies investigating Shmt1 disruption and NTDs, female mice were randomly assigned at weaning to experimental AIN93G diets containing folic acid (C) or AIN93G lacking folic acid (FD) (FIG. 2) and including 0.6% uridine (Rudolph F B & Van Buren C T (1993), which is hereby incorporated by reference in its entirety), 0.2% thymidine (Iwasa et al., "The Well-Balanced Nucleoside-Nucleotide Mixture '0G-VI' for Special Medical Purposes," *Nutrition* 13(4):361-364 (1997), which is hereby incorporated by reference in its entirety), or 0.1% 2'-Deoxyuridine supplementation (Dyets, Bethlehem, Pa.). Diets were assigned with these abbreviations: AIN-93G as control ("C"); Folate Deficient ("FD"), C+ supplemented with 0.6% uridine ("C+U"), C+ supplemented with 0.2% thymidine ("C+T"), C+ supplemented with 0.1% 2'-Deoxyuridine ("C+dU"), FD+ supplemented with 0.6% uridine ("FD+U"), FD+ supplemented with 0.2% thymidine ("FD+T"), FD+ supplemented with 0.1% 2'-Deoxyuridine ("FD+dU").

For all studies, mouse dams were maintained on diet from weaning throughout the breeding period and for the duration of gestation, until killed. Virgin female mice aged 70-120 days were housed overnight with males. The following morning, females were examined for the presence of a vaginal plug. Nine o'clock a.m. the day of the plug appearance was designated as gestational day 0.5 (E0.5). Pregnant females were sacrificed by cervical dislocation at E11.5 and blood was collected by cardiac puncture. Gravid uteri were removed and all implants and resorption sites were recorded. Embryos were examined for presence of NTDs and measured for crown-rump length. All yolk sacs were collected for subsequent genotyping. Embryos were extracted at E11.5 and rapidly frozen in liquid nitrogen followed by storage at −80° C. for biochemical analyses. Embryos examined for morphological abnormalities were derived at E11.5, and fixed in 10% neutral buffered formalin.

Example 3

Genotype Analysis

Genotyping for the sex was performed using established protocols (Clapcote et al., "Simplex PCR Assay for Sex Determination in Mice," *Biotechniques* 38(5):702, 704, 706 (2005); Machado et al., "Diabetic Embryopathy in C57BL/6J. Mice. Altered Fetal Sex Ratio and Impact of the Splotch Allele," *Diabetes* 50(5):1193-1199 (2001); McClive et al., "Rapid DNA Extraction and PCR-Sexing of Mouse Embryos," *Mol. Reprod. Dev.* 60(2):225-226 (2001), which are hereby incorporated by reference in their entirety). Genotyping for Shmt1+/+Shmt1−/− and Shmt1+/− alleles was performed using a previously described protocol (MacFarlane et al., "Cytoplasmic Serine Hydroxymethyltransferase Regulates the Metabolic Partitioning of Methylenetetrahydrofolate but is Not Essential in Mice," *J. Biol. Chem.* 283(38):25846-25853 (2008), which is hereby incorporated by reference in its entirety).

Example 4

Immunoblotting

Total protein was extracted and quantified from frozen tissue. Western blot analyses were performed in at least in triplicate using 15-30 µg of protein extracted from individual maternal livers and embryos. Total soluble protein were separated by 4-12% Bis-Tris gradient SDS-polyacrylamide electrophoresis and transferred to a nitrocellulose membrane. The primary antibodies were diluted in blocking buffer for fluorescent western blotting (Rockland, Pa.) as follows: monoclonal rabbit anti-mouse thymidylate synthase (TYMS) (Cell signaling, 1:1000), monoclonal mouse anti-rabbit TK1 (Abcam, 1:500), polyclonal rabbit anti-mouse Pax3 (Abcam 1:500), polyclonal sheep anti-mouse SHMT1 (1:20,000) (Liu et al., "Lack of Catalytic Activity of a Murine mRNA Cytoplasmic Serine Hydroxymethyltransferase Splice Variant: Evidence Against Alternative Splicing as a Regulatory Mechanism," *Biochemistry* 40(16):4932-4939 (2001), which is hereby incorporated by reference in its entirety), monoclonal anti-mouse p-p53 (Cell signaling, 1:1,000), rabbit monoclonal to HPRT (Acbam, 1:10,000), rabbit polyclonal anti-RRMI (Thermo Scientific, 1:1,000), MTHFD (ref), rabbit polyclonal to UNG2 (Abcam 1:1,000), rabbit polyclonal to HPRT (Abcam 1:10,000) monoclonal rabbit anti-mouse beta-Actin (Cell signaling, 1:1,000), monoclonal mouse anti-mouse beta-Actin (Cell signaling, 1:1,000). Appropriate secondary antibodies were applied: an IRDye800/700-labeled donkey anti-mouse IgG, IRDye800/700-labeled donkey anti-rabbit IgG and IRDye800-labeled donkey anti-sheep IgG secondary antibodies (all in 1:20,000).

Bands were visualized using an Odyssey infrared scanner (Li-Cor) and densitometric analysis of Western blots was performed using Odyssey software. Values were normalized to anti-mouse or anti-rabbit beta-Actin. Densitometric data are presented relative to the mean of wild-type animals fed the control diet.

Example 5

Analysis of Plasma Folate Levels

Folate levels in plasma samples were quantified using a *Lactobacillus casei* microbiological assay as previously described (Suh et al., "Purification and Properties of a Folate-Catabolizing Enzyme," *J. Biol. Chem.* 275(45):35646-35655 (2000), which is hereby incorporated by reference in its entirety).

Example 6

Uracil Content in Nuclear DNA

DNA was extracted from 25-50 mg of liver tissue using DNeasy Tissue and Blood Kit (Qiagen), including an incubation with RNase A (Sigma) and Rnase T1 (Ambion) for 30 min at 37° C. 10 µg of DNA was treated with 1U of uracil DNA glycosylase (Epicentre) for one hour at 37° C. Immediately following incubation, 10 pg of [15N2]Uracil (Cambridge Isotopes) was added to each sample as an internal standard and the sample was dried completely in a desiccators. 50 µl acetonitrile, 10 µl triethylamine, and 1 µl 3,5-bis(trifluormethyl)benzyl bromide were added to each sample and incubated for 25 min at 30° C. with shaking at 500 rpm. 50 µl water followed by 100 µl isooctane were added to each sample. Samples were vortexed and centrifuged. Organic extraction of derived uracil was completed by the removal of the aqueous phase and analysis of the organic phase. Uracil content in nuclear DNA was analyzed by gas chromatography mass spectrometry, as previously described (MacFarlane et al., "Cytoplasmic Serine Hydroxymethyltransferase Regulates the Metabolic Partitioning of Methylenetetrahydrofolate but is Not Essential in Mice," *J. Biol. Chem.* 283(38):25846-25853 (2008), which is hereby incorporated by reference in its entirety).

Example 7

Quantification of Plasma Uridine, Deoxyuridine, and Thymidine

Plasma from mice was collected and kept frozen in −80 C until analysis by high performance liquid chromatography with UV detection. 50 µl of plasma was diluted with an equal volume of 50 mM Ammonium Acetate pH5.6 and spiked with 10 µM 5-fluoruridine as an internal standard. The diluted plasma was clarified using an Amicon Ultra centrifugal filter with a MWCO of 3,000 Kd and centrifuged at 16,000 RPM for 30 minutes. The flow through was collected and 20 µl was injected into a Suppelco Supelcosil LC 18-T 25 cm×4.6 mm 5µ column using a binary buffer system at 1 ml/minute. Buffer A consisted of 100 mM Ammonium Acetate pH 5.6 and buffer B was 100 mM Ammonium Acetate and 20% methanol. The nucleotides were eluded with a linear gradient from 1- to 30 minutes starting with 0% Buffer B to 75% at 30 min, followed by a linear gradient from 30 to 35 min decreasing from 75% to 0% Buffer B. Uridine, Deoxyuridine, and Thymidine levels were quantified by using a Shimadzu Diode array Detector with a starting wavelength of 240 and ending at 300 nm and analyzed using a five point standard curve for each analyte and the internal standard.

Example 8

Mouse Blood Glucose Measurements

Blood glucose levels from non-fasted female mice was recorded on 11.5-12.5$^{th}$ day of gestation. Blood samples were obtained from the tail of each mouse. The tip of the tail was cleaned with spirit before being cut with a sharp blade and 10-20µl of blood collected. The blood glucose levels were measured using an OneTouch®UltraMini® glucose meter (LifeScan, Inc.) and OneTouch® Ultra Blue Test Strips (LifeScan, Inc.). One glucose measurement required approximately 3 µL of blood. Glucose measurements were taken in duplicate and averaged. The statistical analysis was performed by using analysis of variance (ANOVA) for the comparison of data between different experimental groups.

Example 9

Statistical Analyses

Analysis of NTD incidence, including differences between Genotypes, Diets, and interactions of Diet×genotype were analyzed by 2-factor ANOVA by using Tukey's honestly significant difference for post hoc analysis.

Analysis of embryonic CR length, total litter resorptions and implants was analyzed by 2-factor ANOVA with Tukey's honestly significant difference for post hoc analysis, in which litter was considered as a random effect. Independent variables included maternal genotype and diet. Resorption rate was calculated as the ratio of resorptions/total implants per litter and log-transformation was applied to normalize the data. Chi-squared analyses were used to assess any deviation from expected genotype ratios based on Mendelian inheritance. Analysis of uracil concentration, Thymidine, deoxyuridine, glucose and folate were conducted by 2-factor ANOVA with Tukey honestly significant differences for post hoc analysis. Independent variables included maternal genotype and diet. All test were performed in JMP version 8.02 (SAS institute). Western blots analyses were assessed using ANOVA and Dunnett's Multiple Comparison Test. Groups were considered significantly different when the P value was ≤0.05. All statistics were performed using GraphPad Prism version 4.00 for Windows, GraphPad Software, San Diego Calif. USA.

Example 10

Dietary Nucleosides Modify Risk for Folate-Responsive NTDs

Initially, the effect of maternal dietary folic acid on NTD incidence in the Shmt1 mouse model was confirmed. $Shmt1^{+/-}$ males were crossed with 8 week-old $Shmt1^{+/+}$ or $Shmt1^{-/-}$ female mice that were weaned and maintained on one of eight AIN-93G diets described in (FIG. 2). Maternal dietary folic acid significantly affected NTDs occurrence for $Shmt1^{-/-}$ genotype (P<0.0001) and did not affect in $Shmt1^{+/+}$ genotype (P=0.21 NS). Exencephaly was observed in litters from dams maintained on the FD diet (P=0.037, FIG. 3) compared to dams maintained on C diet. This confirms previously published results demonstrating that embryonic Shmt1 disruption was responsive to maternal folate status, as observed in humans and published previously (Beaudin et al., "Insights into Metabolic Mechanisms Underlying Folate-Responsive Neural Tube Defects: A Minireview," *Birth Defects Res. A Clin. Mol. Teratol.* 85(4): 274-284 (2009); Beaudin et al., "Shmt1 and De Novo Thymidylate Biosynthesis Underlie Folate-Responsive Neural Tube Defects in Mice," *Am. J. Clin. Nutr.* 93(4):789-798 (2011), which are hereby incorporated by reference in their entirety). Exencephaly was observed for $Shmt1^{-/-}$ dams (10.6%; 5 NTDs of 47 viable embryos) on the folic acid deficient diets, whereas no NTDs were observed in litters derived from $Shmt1^{-/-}$ female mice isolated from dams fed the C diet. A single embryo with exencephaly (2.4%) was observed from crosses involving $Shmt1^{+/+}$ dams fed the FD diet. All NTD-affected embryos lacked at least one Shmt1 allele from crosses involving $Shmt1^{-/-}$ dams fed the FD diet.

The number of observed $Shmt1^{+/+}$ $Shmt1^{-/-}$ and $Shmt1^{+/-}$ embryos at E11.5 or E12.5 did not deviate from expected values for any of the crosses examined. However, previously published observations (Beaudin et al., "Shmt1 and De Novo Thymidylate Biosynthesis Underlie Folate-Responsive Neural Tube Defects in Mice," *Am. J. Clin. Nutr.* 93(4):789-798 (2011), which is hereby incorporated by reference in its entirety) that maternal diet and embryonic Shmt1 genotype significantly affected embryonic growth at E11.5 were confirmed (Table 2; FIG. 3). Embryos isolated from dams fed a FD diet were significantly shorter from embryos from dams fed C diet ($\chi^2$=4.9669, P<0.0001). Neither weight of female mice or number of implantation sites was significantly affected by any diet or genotype. However, the FD diet resulted in significantly higher rate of resorptions per litter compared to C diet (P<0.05).

Maternal Thymidine Supplementation of FD Diet did not Prevent NTDs Occurrence:

Thymidine supplementation of FD died did not prevent NTD occurrence. Embryos with NTDs were uncovered from both crosses involving $Shmt1^{+/+}$ (2 NTDs 4.1% out of 49) and $Shmt1^{-/-}$ (3 NTDs 9.4% out of 32) dams fed $FD^+$ T diet. Moreover, occurrence of one $Shmt1^{+/+}$ embryo with exencephaly that was uncovered from crosses involving $Shmt1^{+/+}$ dams fed the FD+T diet (Table 3; FIG. 4) are reported. No NTDs were uncovered from dams fed C+T diet. Thymidine supplementation of C diet resulted in significantly lower rate of resorptions per litter compared to C diet (P<0.05).

Maternal Deoxyuridine Supplementation Prevented NTDs in Shmt1 Dams:

Surprisingly, embryos derived from crosses of $Shmt1^{+/+}$ and $Shmt1^{-/-}$ dams fed the folic acid deficient, deoxyuridine supplemented diets (FD+DU) did not exhibit NTDs (Table 3; FIG. 4). Embryos isolated form $Shmt1^{+/+}$ dams fed a C diet were significantly larger than embryos isolated from $Shmt1^{+/+}$ dams fed C+dU (P<0.05, Tukeys honestly significant difference for post hoc analysis, FIG. 3). Neither implantation, dead embryos occurrence, or rates of resorption were significantly different when comparing litters from dams fed FD+U, or C+dU or the C diet. Dams fed the FD+dU and C+dU diets presented with a higher number of dead embryos, but the differences did not reach significance. High frequency of numerous lymphoid aggregates on colons of female mice weaned on C+dU and FD+dU were observed compared to other groups. Edematous of internal organs (up to 4 mice from dU and dUFD groups together), blood in GI track and uterus, and discoloration of pancreas was also observed.

Maternal Uridine Supplementation did not Prevent NTDs in Shmt1 Dams:

The highest frequency of exencephaly was observed in embryos isolated from $Shmt1^{-/-}$ dams fed on FD+U diet (15.9%, 7 of 44 viable embryos; P=0.042) compared to mice fed on C diet. The number of NTDs isolated from $Shmt1^{-/-}$ dams fed FD+U diet was significantly greater compared to embryos isolated from $Shmt1^{-/-}$ dams fed the C diet (P=0.048). Interestingly, increased frequency of exencephaly was also observed (5.4%; 3 out of 56) for $Shmt1^{+/+}$ female mice fed on FD+U diet. This indicates that uridine causes NTDs regardless of Shmt1 genotype. The frequency of exencephaly isolated form FD+U dams was significantly higher (P=0.0021) compared to NTD isolated from dams on C diet.

Exencephaly was observed in litters from both $Shmt1^{-/-}$ (3 NTDs 6% out of 50 viable embryos) and $Shmt1^{+/+}$ (4 NTDs 5.8% out of 69) dams. There were significantly more NTD-affected embryos in dams fed the C diet compared to the C+U (P=0.048). These findings demonstrate that dietary uridine causes NTDs independent of Shmt1 genotype and maternal folate status. One $Shmt1^{+/+}$ embryo each with exencephaly was isolated from $Shmt1^{+/+}$ dams fed the FD+U and C+U diets (Table 3; FIG. 4). Neither genotype nor diets significantly affected the weight of female mice at onset of gestation.

Example 11

Shmt1+/+ and Shmt1−/− Mice Exhibit Altered Plasma Folate Levels and Blood Glucose Levels The effect of Shmt1 genotype on plasma folate concentrations was determined for $Shmt1^{+/+}$ and $Shmt1^{-/-}$ mice.

Plasma folate levels were significantly lower in animals dams fed the folic acid deficient diet (F=58.3526, P<0.0001; FIG. 5). Furthermore, Shmt1$^{+/+}$ and Shmt1$^{-/-}$ mice weaned to the C+T and C+dU diets, but not C+U diets, exhibited significantly higher levels of plasma folate compared to Shmt1$^{+/+}$ mice fed the control diet (P<0.05; FIG. 5).

Mice fed uridine supplemented diets exhibited higher blood glucose levels (P<0.05). Blood glucose was elevated in both genotypes in dams fed C+U and FD+U diets. Interestingly, dams fed on dU supplemented diets had similar blood glucose levels (Table 4; FIG. 5).

Example 12

Shmt1 Disruption and Nucleotide Supplementation Did not Increase Uracil Misincorporation in Maternal Liver DNA and Other Metabolites Neither dietary folic acid nor nucleotides affected maternal uracil levels in liver nuclear DNA after consuming the diets for 6 weeks, suggesting that uracil is not a biomarker for NTDs in liver DNA. However, Shmt1−/− mice fed on FD tended to have increased uracil incorporation in DNA relative Shmt1+/+ mice C diet. In general, uracil levels were significantly increased in response to maternal Shmt1 disruption only (F=6.7414; P=0.0114; average uracil levels of Shmt1−/− were 0.22±0.01; average uracil levels of Shmt1+/+0.19±0.01 (Mean±SEM).

Example 13

Deoxyduridine Supplementation Prevents NTDs in Response to Maternal Folate Deficiency in Mice with Shmt1 Disruption It was established that cytoplasmic serine hydroxymethyltransferase ("SHMT1") acts as a metabolic switch that regulates the partitioning of one-carbon units between the dTMP and methionine biosynthetic pathways (FIG. 1) (Herbig et al., "Cytoplasmic Serine Hydroxymethyltransferase Mediates Competition Between Folate-Dependent Deoxyribonucleotide and S-Adenosylmethionine Biosyntheses," *J. Biol. Chem.* 277(41):38381-38389 (2002), which is hereby incorporated by reference in its entirety). Folate-activated one-carbons can be derived in the cytoplasm from formate through the Mthfd1 gene product or from serine through SHMT1 to support methionine and thymidylate biosynthesis (FIG. 1). Thymidylate synthesis can occur in both the cytoplasm and nucleus (Woeller et al., "Evidence for Small Ubiquitin-Like Modifier-Dependent Nuclear Import of the Thymidylate Biosynthesis Pathway," *J. Biol. Chem.* 282 (24):17623-17631 (2007), which is hereby incorporated by reference in its entirety). When expressed, SHMT1 preferentially partitions methylenetetrahydrofolate (methyleneTHF) into the dTMP synthesis pathway through the small ubiquitin-like modifier (SUMO)-mediated compartmentalization of the dTMP biosynthetic pathway components in the nucleus during S-phase (Herbig et al., "Cytoplasmic Serine Hydroxymethyltransferase Mediates Competition Between Folate-Dependent Deoxyribonucleotide and S-Adenosylmethionine Biosyntheses," *J. Biol. Chem.* 277(41):38381-38389 (2002); Woeller et al., "Evidence for Small Ubiquitin-Like Modifier-Dependent Nuclear Import of the Thymidylate Biosynthesis Pathway," *J. Biol. Chem.* 282(24):17623-17631 (2007), which are hereby incorporated by reference in their entirety). In the cytoplasm, SHMT1 tightly binds and sequesters 5-methyl-THF making it unavailable for the methionine cycle, inhibiting AdoMet synthesis and reducing the cellular methylation potential (Herbig et al., "Cytoplasmic Serine Hydroxymethyltransferase Mediates Competition Between Folate-Dependent Deoxyribonucleotide and S-Adenosylmethionine Biosyntheses," *J. Biol. Chem.* 277(41):38381-38389 (2002), which is hereby incorporated by reference in its entirety).

As noted above, folates function as enzyme cofactors that carry and chemically activate one-carbons for a network of anabolic pathways collectively known as one-carbon metabolism. OCM is essential for de novo purine and thymidylate (dTMP) biosynthesis, and for the remethylation of homocysteine to methionine. Methionine can be adenosylated to form S-adenosylmethionine (AdoMet), a methyl donor for numerous cellular methylation reactions (FIG. 1). Responsiveness to maternal folate supplementation has been determined in only a few of the 150 mouse models (Harris et al., "Mouse Mutants With Neural Tube Closure Defects and Their Role in Understanding Human Neural Tube Defects," *Birth Defects Res. A Clin. Mol. Teratol.* 79(3): 187-210 (2007), which is hereby incorporated by reference in its entirety) that exhibit NTDs (Wlodarczyk et al., "Spontaneous Neural Tube Defects in Splotch Mice Supplemented with Selected Micronutrients," *Toxicol. Appl. Pharmacol.* (2005); Fleming et al., "Embryonic Folate Metabolism and Mouse Neural Tube Defects," *Science* 280(5372):2107-2109 (1998); Barbera et al., "Folic Acid Prevents Exencephaly in Cited2 Deficient Mice," *Hum. Mol. Genet.* 11(3):283-293 (2002); Carter et al., "Crooked Tail (Cd) Models Human Folate-Responsive Neural Tube Defects," *Hum. Mol. Genet.* 8(12):2199-2204 (1999), which are hereby incorporated by reference in their entirety), and, of those, two NTD models that respond to exogenous folic acid. The splotch mutant (Pax3$^{Sp}$) has demonstrated impairments in OCM. NTDs in the splotch mutant can be rescued with supplemental dietary folic acid or thymidine, indicating that folic acid prevents NTDs by rescuing de novo thymidylate synthesis in this mouse model (Wlodarczyk et al., "Spontaneous Neural Tube Defects in Splotch Mice Supplemented with Selected Micronutrients," *Toxicol. Appl. Pharmacol.* (2005); Fleming et al., "Embryonic Folate Metabolism and Mouse Neural Tube Defects," *Science* 280(5372):2107-2109 (1998), which are hereby incorporated by reference in their entirety). Embryonic serine hydroxymethyltransferase 1 (encoded by Shmt1) disruptions also caused folate-responsive NTDs in mice.

This is the first model with a genetic disruption in the folate metabolism pathway that results in folic-acid responsive NTDs (Beaudin et al., "Shmt1 and De Novo Thymidylate Biosynthesis Underlie Folate-Responsive Neural Tube Defects in Mice," *Am. J. Clin. Nutr.* 93(4):789-798 (2011), which is hereby incorporated by reference in its entirety). This gene-diet interaction closely resembles the interactions found in human studies of NTD pathogenesis (Relton et al., "Low Erythrocyte Folate Status and Polymorphic Variation in Folate-Related Genes are Associated with Risk of Neural Tube Defect Pregnancy," *Mol. Genet. Metab.* 81(4):273-281 (2004); Christensen et al., "Genetic Polymorphisms in Methylenetetrahydrofolate Reductase and Methionine Synthase, Folate Levels in Red Blood Cells, and Risk of Neural Tube Defects," *Am. J. Med. Genet.* 84(2):151-157 (1999), which are hereby incorporated by reference in their entirety). Shmt1 is responsible for generating one-carbon units from the enzymatic cleavage of serine to glycine that are preferentially shunted to thymidylate biosynthesis. Shmt1$^{-/-}$ and Shmt1$^{+/-}$ mice are sensitized to folate-responsive NTDs, and demonstrate impaired de novo thymidylate biosynthesis, and therefore provide a means to study gene-nutrient interactions in NTDs (Beaudin et al., "Shmt1 and De Novo Thymidylate Biosynthesis Underlie Folate-Responsive Neural Tube Defects in Mice," *Am. J. Clin. Nutr.* 93(4):789-798 (2011), which is hereby incorporated by reference in its entirety). However, Shmt1 is not essential in mice due to functional redundancy provided by Shmt2 expression (MacFarlane et al., "Cytoplasmic Serine Hydroxymethyltransferase Regulates the Metabolic Partitioning of Methylenetetrahydrofolate but is Not Essential in Mice," *J. Biol. Chem.* 283(38): 25846-25853 (2008), which is hereby incorporated by reference in its entirety). The mechanisms whereby disruption of de novo thymidylate biosynthesis causes NTDs in the Shmt1 mouse model is not known. One study indicated that dietary thymidine supplementation prevented NTDs in splotch homozygotes (Fleming et al., "Embryonic Folate Metabolism and Mouse Neural Tube Defects," *Science* 280(5372):2107-2109 (1998), which is hereby incorporated by reference in its entirety), while others were not able to able to demonstrate NTD prevention with thymidine.

Folic acid prevents the occurrence and recurrence of neural tube closure defects (NTDs), but causal metabolic pathways underlying folic acid-responsive NTDs are still not well understood. As noted above, previously, it was shown that disruption of the gene encoding serine hydroxymethyltransferase 1 (Shmt1) sensitizes mice to folic-acid responsive NTDs, implicating the de novo thymidylate biosynthesis pathway and DNA synthesis in the etiology of folic-acid responsive NTDs. To better understand the mechanisms of folic acid in NTD prevention, the ability of dietary uridine, thymidine, and deoxyuridine supplementation to rescue NTDs when present in the maternal diets of $Shmt1^{-/-}$ mice was examined. It is demonstrated in the Examples above that dietary deoxyuridine, but not thymidine prevented NTDs in response to maternal folate deficiency. Surprisingly, uridine supplementation exacerbated NTD frequency independent of dietary folic acid and increased maternal glucose. The presence of these nucleosides in the diet did not affect uracil accumulation in nuclear DNA, but markedly affect Pax3 levels in embryos, providing a new mechanism whereby impairments in one-carbon metabolism increase risk for NTDs.

More particularly, the ability of dietary nucleosides (0.6% uridine, 0.2% thymidine and 0.1% 2'-deoxyuridine) to modify NTD risk in $Shmt1^{-/-}$ dams fed a folate-deficient AIN93G diet was examined. It was hypothesized that dietary thymidine would prevent NTDs if a lack of cellular thymidylate was causing NTDs, whereas dietary uridine and/or deoxyuridine would increase NTD incidence if the accumulation of these nucleosides/nucleotides caused NTDs in the $Shmt1^{-/-}$ mouse model. The results shown in the Examples set forth above demonstrate that maternal dietary deoxyuridine, but not thymidine, prevents NTDs in folate deficient $Shmt1^{-/-}$ dams, whereas dietary uridine causes NTDs independent of Shmt1 genotype and maternal folate status. These findings provide new insights into the mechanisms of folic acid-responsive NTDs in humans.

Example 14

Mice

SHMT1 null ($Shmt1^{-/+}$) mice were generated as previously described (MacFarlane et al., "Cytoplasmic Serine Hydroxymethyltransferase Regulates the Metabolic Partitioning of Methylenetetrahydrofolate but is Not Essential in Mice," *J. Biol. Chem.* 283(38):25846-25853 (2008), which is hereby incorporated by reference in its entirety) and backcrossed a minimum of 10 generations onto the C57BL/6J strain. Mice were genotyped using the forward primer 5'-GACACTGTTCACATCCCTC-3' (SEQ ID NO:1) and the reverse primer 5'-CAAAACATTCGGGAGCCTC-3' (SEQ ID NO:2). The forward primer corresponds to an intron 6 sequence located 5' to a loxP site and exon 7 and the reverse primer corresponds to an intron 7 sequence located downstream of a 3' loxP site (MacFarlane et al., "Cytoplasmic Serine Hydroxymethyltransferase Regulates the Metabolic Partitioning of Methylenetetrahydrofolate but is Not Essential in Mice," *J. Biol. Chem.* 283(38):25846-25853 (2008), which is hereby incorporated by reference in its entirety). C57BL/6J-$Apc^{Min}$/J ($Apc^{min/+}$) mice were obtained. Genotyping of $Apc^{min/+}$ mice was performed using the following primers recommended by The Jackson Laboratory protocol: wild-type forward primer 5'-GCCATCCCTTCACGTTAG-3' (SEQ ID NO:3), Min forward primer 5'-TTCTGAGAAAGACAGAAGTTA-3' (SEQ ID NO:4), and a common reverse primer 5'-TTCCACTTTGGCATAAGGC-3' (SEQ ID NO:5). $Shmt1^{-/+}$ mice were mated to $Apc^{min/+}$ mice. Double heterozygous offspring were intercrossed to achieve $Apc^{min/+}Shmt1^{+/+}$, $Apc^{min/+}Shmt1^{-/+}$ or $Apc^{min/+}Shmt1^{-/-}$ mice.

Example 15

Diets

Mice were randomly weaned onto either a control (AIN-93G; Dyets, Inc.) diet supplemented with 0.1% deoxyuridine, or a modified AIN-93G diet lacking folic acid, a modified AIN-93G diet lacking folic acid supplemented with 0.1% deoxyuridine, a modified AIN-93G diet lacking folic acid supplemented with 0.2% thymidine, or a modified AIN-93G diet lacking folic acid supplemented with 0.6% uridine (Dyets, Inc.) at 3 weeks of age. The control diet contained 2 mg/kg folic acid, and the folatedeficient diet contained 0 mg/kg folic acid. Mice were maintained on the diet for 5 weeks ($Apc^{+/+}$) or 11 weeks ($Apc^{min/+}$).

Example 16

Tumor Assessment

The small intestine and colon were removed, flushed with cold PBS, opened longitudinally, and laid flat lumen side up for examination using a dissecting microscope as previously described (Chiu et al., "Sulindac Causes Rapid Regression of Preexisting Tumors in Min/+Mice Independent of Prostaglandin Biosynthesis," *Cancer Res.* 57:4267-73 (1997), which is hereby incorporated by reference in its entirety). Tumors were counted according to intestinal location (small intestine or colon) and their diameter measured by a pathologist-trained investigator who was blinded to the genotype of the intestinal specimen. Tumor load is a function of tumor number and area and was calculated as the total tumor area per mouse.

Example 17

Plasma and Tissue Folate Determination

Folate concentration of plasma and tissues was quantified using the *Lactohacislus casei* microbiological assay (Herbig et al., "Cytoplasmic Serine Hydroxymethyltransferase Mediates Competition Between Folate-Dependent Deoxyribonucleotide and S-Adenosylmethionine Biosyntheses," *J. Biol. Chem.* 277(41):38381-38389 (2002), which is hereby incorporated by reference in its entirety). Protein concentration was quantified (Bensadoun et al., "Assay of Proteins in the Presence of Interfering Materials," *Anal. Biochem.* 70:241-50 (1976), which is hereby incorporated by reference in its entirety).

Example 18

Detection of Uracil in Nuclear DNA

Uracil content in hepatic nuclear DNA was determined by gas chromatography/mass spectrometry as previously described (MacFarlane et al., "Cytoplasmic Serine Hydroxymethyltransferase Regulates the Metabolic Partitioning of Methylenetetrahydrofolate but is Not Essential in Mice," *J. Biol. Chem.* 283(38):25846-25853 (2008), which is hereby incorporated by reference in its entirety). Uracil content in liver nuclear DNA has been shown to correlate with uracil content in colonic nuclear DNA in $Shmt1^{-/+}$ mice.

Example 19

Uridine Supplementation Treats Intestinal Tumors

It was shown that Shmt1 hemizygosity was associated with increased risk for intestinal cancer in $Apc^{min/+}$ mice through a gene-by-diet interaction, indicating that the capacity for thymidylate synthesis modifies susceptibility to intestinal cancer in $Apc^{min/+}$ mice MacFarlane et al., "Shmt1 Heterozygosity Impairs Folate-Dependent Thymidylate Synthesis Capacity and Modifies Risk of $Apc^{min}$-Mediated Intestinal Cancer Risk," *Cancer Res.* 71:2098-2107 (2011), which is hereby incorporated by reference in its entirety. That study was repeated in wild type except that diets were supplemented with 0.6% uridine 0.2% thymidine or 0.1% deoxyuridine. The results summarized in FIG. 6 show that uridine supplementation treats intestinal tumors in mice.

In particular, the effects of dietary deoxyuridine (0.1% added to an AIN93G diet lacking folic acid) and uridine (0.6% added to an AIN93G diet lacking folic acid) on tumor number in a mouse model of intestinal tumorigenesis (Apc-min) were examined following the same protocol described previously (MacFarlane et al., "Shmt1 Heterozygosity Impairs Folate-Dependent Thymidylate Synthesis Capacity and Modifies Risk of $Apc^{min}$-Mediated Intestinal Cancer Risk," *Cancer Res.* 71:2098-2107 (2011), which is hereby incorporated by reference in its entirety). Apc-min mice fed the AIN93G diet lacking folic acid exhibited (35+/−5) intestinal tumors, whereas those fed the AIN-93G diet lacking folic acid but supplemented with uridine exhibited (18+/−2) tumors, and those fed the AIN-93G diet lacking folic acid but supplemented with deoxyuridine exhibited (29+/−2.0) tumors. These results demonstrate that uridine supplementation reduced tumor numbers by 49% in this study (p=0.02), whereas supplemental deoxyuridine had no effect on tumor number.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of reducing the risk for development of a folate deficiency-related birth defect in a fetus, said method comprising:
   selecting a mammalian subject, wherein the subject is a pregnant female, lactating female, or female of childbearing age that is attempting to become pregnant, and administering to the selected subject an effective amount of deoxyuridine to reduce the risk for development of a folate deficiency-related birth defect in the fetus.

2. The method according to claim 1, wherein the subject is a human.

3. The method according to claim 1, wherein the subject is a female of childbearing age that is attempting to become pregnant.

4. The method according to claim 1, wherein the deoxyuridine is administered as part of a nutraceutical composition, pharmaceutical composition, functional food, functional nutrition product, medical food, medical nutrition product, or dietary supplement.

5. The method according to claim 1, wherein said administering further comprises:
   administering one or more vitamins, minerals, trace elements, or combinations thereof.

6. The method according to claim 5, wherein the one or more vitamins, minerals, trace elements, or combinations thereof is selected from the group consisting of Vitamin A, Vitamin C, Vitamin D, Vitamin E, Vitamin K, Thiamin, Riboflavin, Niacin, Folate, Vitamin B12, Vitamin B6, Pantothenic Acid, Biotin, Choline, Chromium, Copper, Iodine, Molybdenum, Selenium, Iron, Zinc, Magnesium, and combinations thereof.

7. The method according to claim 1, wherein said administering further comprises:
   administering to the subject folate or derivatives thereof in an amount that is less than about 1000 μg, less than about 400 μg, less than about 300 μg, less than about 200 μg, or less than about 100 μg.

8. The method according to claim 1, wherein said administering further comprises:
   administering to the subject folate or derivatives thereof in an amount at least about 50% less than that recommended as a daily dietary allowance for a woman of childbearing age.

9. The method according to claim 1, wherein the deoxyuridine is administered in capsule, tablet, granule, or lozenge form.

10. The method according to claim 1, wherein said administering is parenteral.

11. The method according to claim 1, wherein said administering is oral.

12. The method according to claim 1, wherein the subject is a pregnant female.

13. The method according to claim 1, wherein the subject is a lactating female.

14. The method according to claim 1, wherein the folate deficiency-related birth defect is a neural tube defect.

* * * * *